(12) United States Patent
Ono et al.

(10) Patent No.: US 10,844,495 B2
(45) Date of Patent: *Nov. 24, 2020

(54) PHOTOCHEMICAL REACTION SYSTEM

(71) Applicant: KABUSHIKI KAISHA TOSHIBA, Tokyo (JP)

(72) Inventors: Akihiko Ono, Tokyo (JP); Satoshi Mikoshiba, Yamato (JP); Yuki Kudo, Yokohama (JP); Jun Tamura, Yokohama (JP); Ryota Kitagawa, Tokyo (JP); Chingchun Huang, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 120 days.

This patent is subject to a terminal disclaimer.

(21) Appl. No.: 15/697,956

(22) Filed: Sep. 7, 2017

(65) Prior Publication Data

US 2017/0370012 A1   Dec. 28, 2017

Related U.S. Application Data

(63) Continuation of application No. 14/717,622, filed on May 20, 2015, now Pat. No. 9,758,882, which is a (Continued)

(30) Foreign Application Priority Data

Nov. 20, 2012   (JP) .................................. 2012-254700

(51) Int. Cl.
*C25B 3/04* (2006.01)
*C01B 32/05* (2017.01)
(Continued)

(52) U.S. Cl.
CPC ............... *C25B 3/04* (2013.01); *B01J 19/127* (2013.01); *C01B 32/05* (2017.08); *C01B 32/50* (2017.08);
(Continued)

(58) Field of Classification Search
None
See application file for complete search history.

(56) References Cited

U.S. PATENT DOCUMENTS 4,364,915 A * 12/1982 Proctor .............. B01D 53/1475
423/219
4,381,978 A    5/1983 Gratzel
(Continued)

FOREIGN PATENT DOCUMENTS

CN     1251209 A     4/2000
CN   102224279 A    10/2011
(Continued)

OTHER PUBLICATIONS

Rees et al, Electrochemical CO2 Sequestration in Ionic Liquids; A Perspective, Energy & Environemental Science, vol. 4, No. 2, Dec. 2010, pp. 403-408 (Year: 2010).*

(Continued)

*Primary Examiner* — Harry D Wilkins, III
(74) *Attorney, Agent, or Firm* — Oblon, McClelland, Maier & Neustadt, L.L.P.

(57) ABSTRACT

According to one embodiment, a photochemical reaction system comprises a $CO_2$ production unit, a $CO_2$ absorption unit, and a $CO_2$ reduction unit. The $CO_2$ reduction unit comprises a laminated body and an ion transfer pathway. The laminated body comprises an oxidation catalyst layer producing $O_2$ and $H^+$ by oxidizing $H_2O$, a reduction catalyst layer producing carbon compounds by reducing $CO_2$ absorbed by the $CO_2$ absorption unit, and a semiconductor
(Continued)

layer formed between the oxidation catalyst layer and the reduction catalyst layer and develops charge separation with light energy. The ion transfer pathways make ions move between the oxidation catalyst layer side and the reduction catalyst layer side.

3 Claims, 19 Drawing Sheets

Related U.S. Application Data continuation of application No. PCT/JP2013/080197, filed on Nov. 8, 2013.

(51) Int. Cl.
| | | |
|---|---|---|
| *C01B 32/50* | (2017.01) | |
| *B01J 19/12* | (2006.01) | |
| *C07C 51/00* | (2006.01) | |
| *C25B 9/06* | (2006.01) | |
| *C25B 9/08* | (2006.01) | |
| *H01L 31/076* | (2012.01) | |
| *C25B 1/00* | (2006.01) | |

(52) U.S. Cl.
CPC .............. *C07C 51/00* (2013.01); *C25B 1/003* (2013.01); *C25B 9/06* (2013.01); *C25B 9/08* (2013.01); *H01L 31/076* (2013.01); *B01J 2219/0875* (2013.01); *B01J 2219/1203* (2013.01); *Y02C 10/06* (2013.01); *Y02E 10/548* (2013.01)

(56) References Cited

U.S. PATENT DOCUMENTS

| | | | | |
|---|---|---|---|---|
| 4,673,473 A * | 6/1987 | Ang | ..................... | C25B 11/035 |
| | | | | 204/263 |
| 6,198,037 B1 | 3/2001 | Nakata | | |
| 9,315,910 B2 * | 4/2016 | Eastman | ................... | C25B 1/04 |
| 2005/0048334 A1 * | 3/2005 | Sridhar | ............. | H01M 8/04201 |
| | | | | 429/418 |
| 2008/0283121 A1 | 11/2008 | Guerra | | |
| 2010/0133111 A1 | 6/2010 | Nocera et al. | | |
| 2010/0193370 A1 * | 8/2010 | Olah | ................... | C07C 29/1518 |
| | | | | 205/450 |
| 2010/0313794 A1 | 12/2010 | Constantz | | |
| 2011/0114502 A1 * | 5/2011 | Cole | ....................... | C25B 1/003 |
| | | | | 205/414 |
| 2011/0315560 A1 * | 12/2011 | Rabaey | ................. | C02F 1/4618 |
| | | | | 205/344 |
| 2013/0026029 A1 * | 1/2013 | Kayaert | ................. | B01J 14/005 |
| | | | | 204/230.8 |
| 2013/0118910 A1 * | 5/2013 | Teamey | .................... | C25B 1/00 |
| | | | | 205/427 |
| 2013/0277209 A1 | 10/2013 | Sato et al. | | |
| 2014/0262792 A1 * | 9/2014 | Rosenthal | ........... | C25B 11/0447 |
| | | | | 205/50 |
| 2018/0265993 A1 * | 9/2018 | Kamire | ..................... | C25B 1/04 |

FOREIGN PATENT DOCUMENTS

| | | |
|---|---|---|
| EP | 0 982 780 A1 | 3/2000 |
| GB | 2414243 A | 11/2005 |
| JP | 10-290017 | 10/1998 |
| JP | 2010-533784 A | 10/2010 |
| JP | 2011-094194 | 5/2011 |
| JP | 2012-505310 | 3/2012 |
| JP | 2012-112001 A | 6/2012 |
| KR | 1020010005549 | 1/2001 |
| WO | 99/038215 | 7/1999 |
| WO | WO 2011/123907 A1 | 10/2011 |
| WO | 2012/077198 | 6/2012 |
| WO | WO 2012/091045 A1 | 7/2012 |

OTHER PUBLICATIONS

Wender, Irving, Reactions of synthesis gas, Fuel Processing Technology, vol. 48, No. 3, Sep. 1996, pp. 189-297 (Year: 1996).*
Zhao et al, Electrochemical reduction of supercritical carbon dioxide in ionic liquid 1-n-butyl-3-methylimidazolium hexafluorophosphate, The Journal of Supercritical Fluids, vol. 32, Nos. 1-3, Dec. 2004, pp. 287-291 (Year: 2004).*
Olah et al, Chemical Recycling of Carbon Dioxide to Methanol and Dimethyl Ether: From Greenhouse Gas to Renewable, Environmentally Carbon Neutral Fuels and Synthetic Hydrocarbons, Journal of Orangic Chemistry, vol. 74, No. 2, Dec. 2008, pp. 487-498 (Year: 2008).*
S. Y. Reece et al., "Wireless Solar Water Splitting Using Silicon-Based Semiconductors and Earth-Abundant Catalysts", vol. 334, Nov. 4, 2011, pp. 645-648.
International Search Report issued in Japanese application No. PCT/JP2013/080197, dated Jan. 14, 2014.
Office Action dated Nov. 24, 2015 in Australian Patent Application No. 2013349016.
Office Action dated Nov. 27, 2015 in Australian Patent Application No. 2013349016.
Notice of Allowance as received in the corresponding Korean Patent Application No. 10-2015-7012798 dated Jun. 30, 2017.
Extended European Search Report dated Jun. 2, 2016 in Patent Application No. 13856366.3.
Office Action dated Jun. 28, 2016 in Japanese Patent Application No. 2012-254700.
Combined Chinese Office Action and Search Report dated Jul. 5, 2016 in Patent Application No. 201380060232.X.
Office Action dated Sep. 27, 2016 in Japanese Patent Application No. 2012-254700.

* cited by examiner

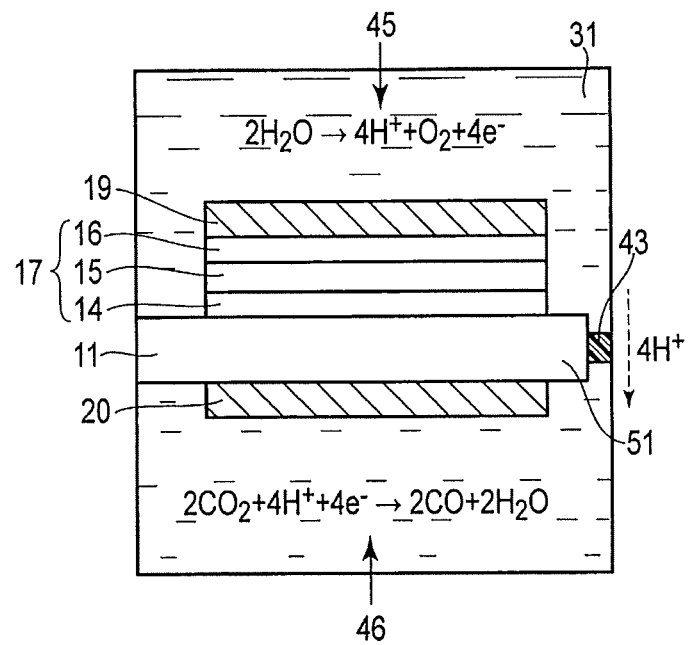
F I G. 5
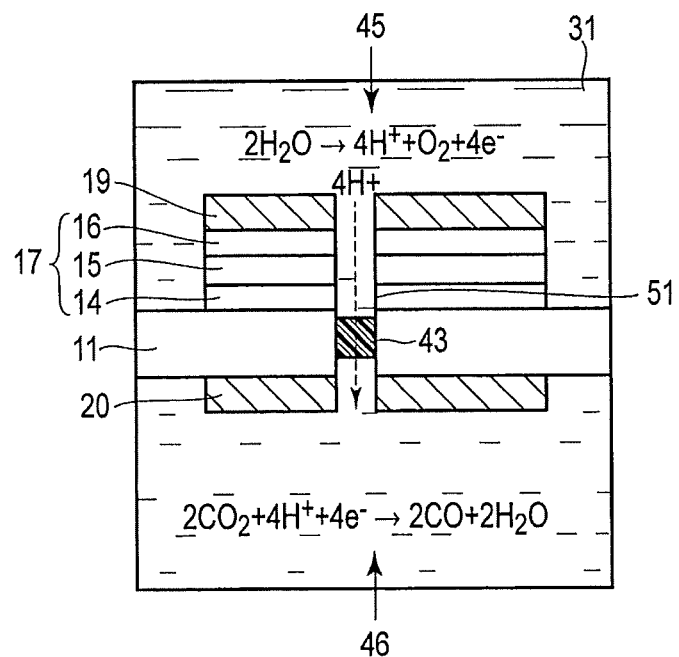
F I G. 6

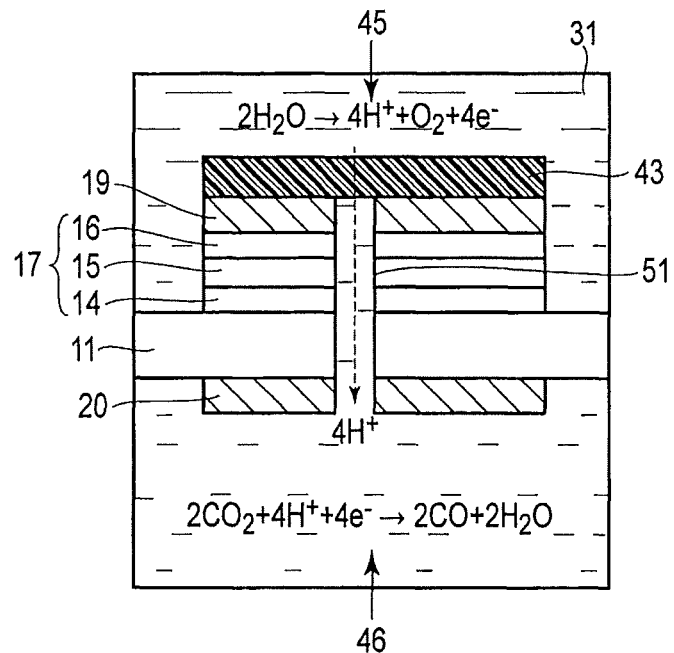
F I G. 7
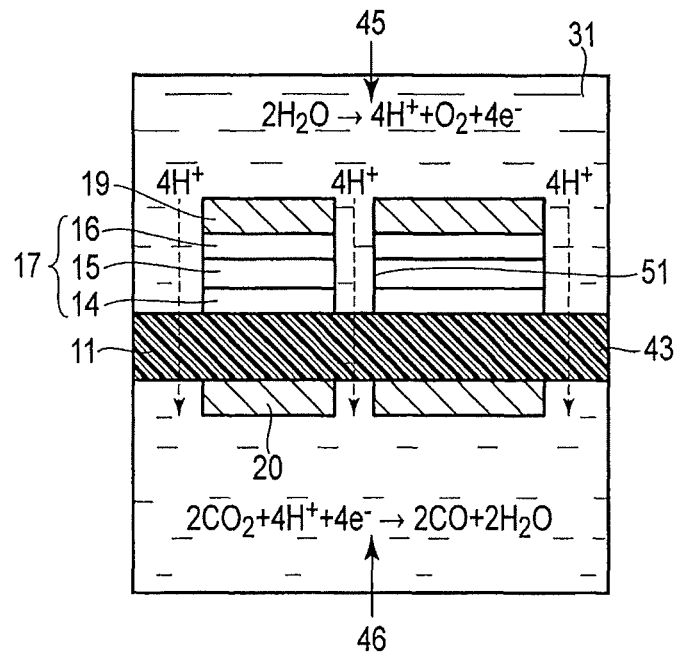
F I G. 8

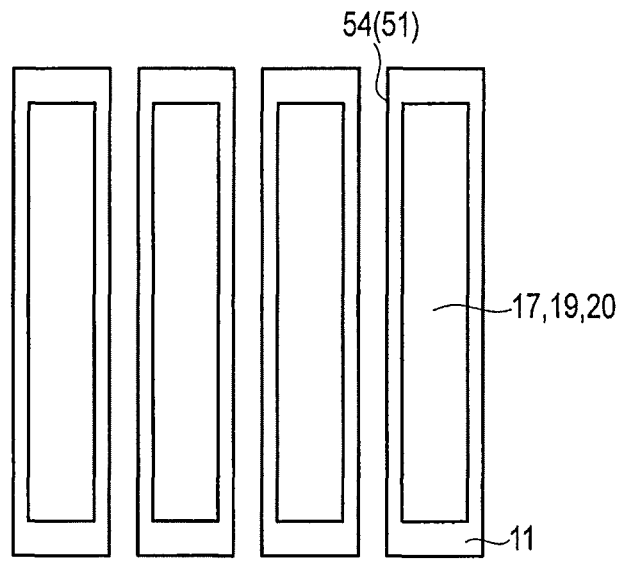
F I G. 11
| Sample cell number | Through-hole equivalent circle diameter($\mu$m) | Through-hole area ratio(%) | Photoreduction efficiency(a.u.) |
|---|---|---|---|
| 1-1 | 50 | 10 | 1.27 |
| 1-2 | 50 | 20 | 1.12 |
| 1-3 | 50 | 30 | 1.05 |
| 1-4 | 50 | 40 | 0.80 |
| 1-5 | 100 | 10 | 1.30 |
| 1-6 | 100 | 20 | 1.19 |
| 1-7 | 100 | 30 | 1.07 |
| 1-8 | 100 | 40 | 0.83 |
| 1-9 | 200 | 10 | 1.33 |
| 1-10 | 200 | 20 | 1.20 |
| 1-11 | 200 | 30 | 1.10 |
| 1-12 | 200 | 40 | 0.87 |
F I G. 12

| Sample cell number | Through-hole equivalent circle diameter($\mu$m) | Through-hole area ratio(%) | Photoreduction efficiency(a.u.) |
|---|---|---|---|
| 2-1 | 0.1 | 30 | 1.19 |
| 2-2 | 0.5 | 30 | 1.72 |
| 2-3 | 1 | 30 | 1.08 |
| 2-4 | 2.0 | 30 | 0.86 |

F I G. 17

| Sample cell number | Gas product in oxidation reactio electrolytic tank | Gas product in reduction reaction electrolytic tank | Photoreduction efficiency(a.u.) |
|---|---|---|---|
| 3-1 | $O_2$ | $H_2$、$CO_2$ | 2.20 |
| 3-2 | $O_2$、$H_2$、$CO_2$ | $O_2$、$H_2$、$CO_2$ | 2.45 |
| Comparative example | $O_2$ | $H_2$、$CO_2$ | 1.00 |

F I G. 18

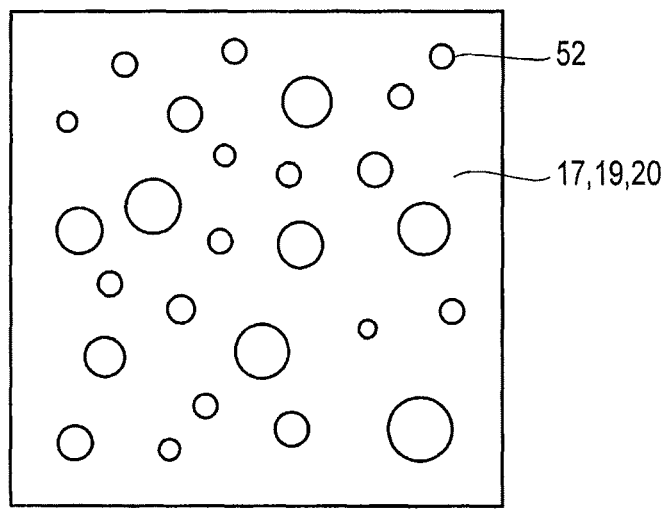
F I G. 19
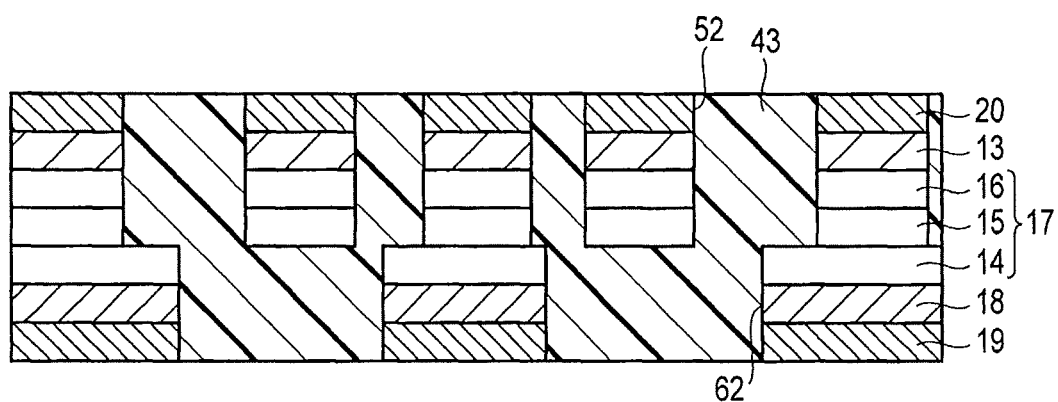
F I G. 20

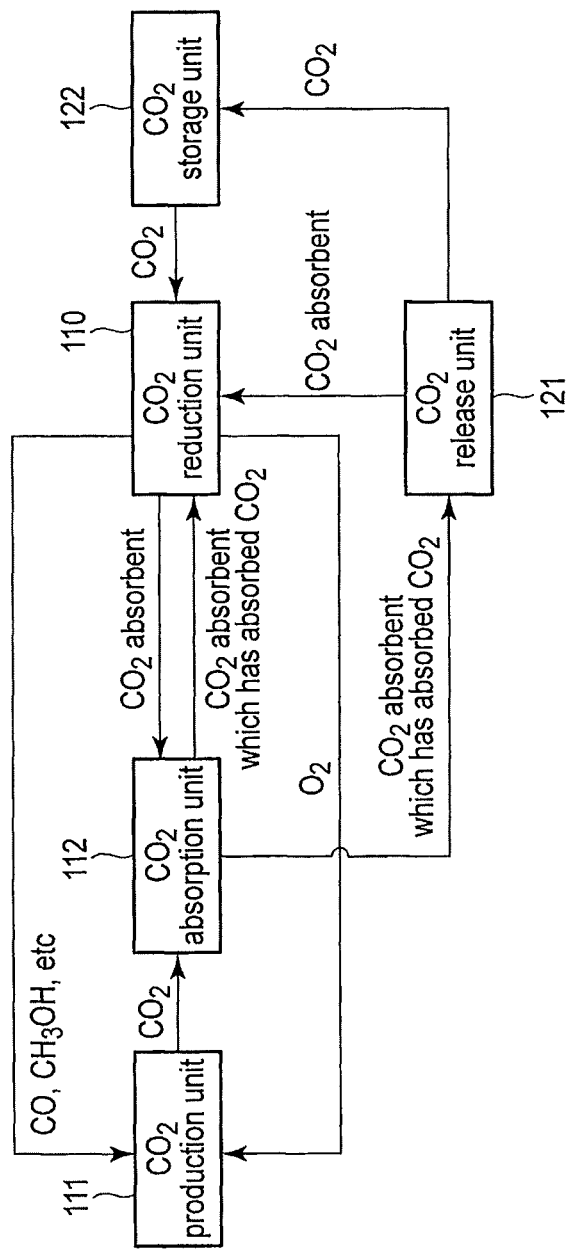
F I G. 35

PHOTOCHEMICAL REACTION SYSTEM

CROSS-REFERENCE TO RELATED APPLICATIONS

This application is Continuation Application of U.S. Ser. No. 14/717,622, filed May 20, 2015, allowed, which is a Continuation Application of PCT Application No. PCT/JP2013/080197, filed Nov. 8, 2013 and based upon and claims the benefit of priority from the prior Japanese Patent Application No. 2012-254700, filed Nov. 20, 2012, the entire contents of each of which are incorporated herein by reference.

FIELD

Embodiments of the present invention relate to a photochemical reaction SYSTEM.

BACKGROUND

Reducing $CO_2$ efficiently by light energy like plants has been required from the standpoint of energy problems and environmental concerns. Plants use a system called the Z-scheme to excite light energy in two stages. Using a photochemical reaction of this system, plants synthesize cellulose and sugar by obtaining electrons from water ($H_2O$) and reducing carbon dioxide ($CO_2$).

However, few technologies that can efficiently dissolve $CO_2$ with electrons obtained from water through artificial photochemical reaction without using any sacrificial reagent are available.

A photochemical reaction device disclosed in JP-A-2011-094194, for example, has an oxidation electrode for producing oxygen ($O_2$) by oxidizing $H_2O$ and a reduction electrode for producing a carbon compound by reducing $CO_2$. The oxidation electrode has an oxidation catalyst for oxidizing $H_2O$ on a surface of a photocatalyst and gains potential with light energy. The reduction electrode has a reduction catalyst for reducing $CO_2$ on a surface of the photocatalyst and is connected to the oxidation electrode with an electric wire. The reduction electrode reduces $CO_2$ to produce formic acid (HCOOH) by gaining reduction potential of $CO_2$ from the oxidation electrode. To gain the potential necessary for reducing $CO_2$ using an optical wavelength and a photocatalyst, the photochemical reaction device thus employs a Z-scheme-type artificial photosynthesis system that imitates plants.

However, Jp-A-2011-094194, the solar energy conversion efficiency is very low at around 0.04%. This is because the energy efficiency of the photocatalyst excited by the optical wavelength is low. Because the reduction electrode is connected with the oxidation electrode with an electric wire, the efficiency in extracting electricity (electric current) decreases due to interconnection resistance, and, as a consequence, the efficiency becomes low.

An device that has a configuration to produce a reaction by catalysts disposed on both sides of a silicon solar cell used for achieving the reaction potential is disclosed in Jp-A-H10-290017. S. Y. Reece, et al., Science. vol. 334. pp. 645 (2011) describes an device which includes layered silicon solar cells for achieving the reaction potential and produces an electrolytic reaction of $H_2O$ by disposing catalysts on both sides of the silicon solar cells. Both of these devices have a very high solar energy conversion efficiency of 2.5%.

These devices are easily configured in a large size because they do not need to be hard-wired. They also have another feature in which a material partition process is not necessary because the cell itself plays a role of a divider plate to insulate materials.

These devices, however, have not succeeded in the reduction reaction of $CO_2$. Such plate-like laminate structure moreover does not take into consideration the fact that, for the $CO_2$ reduction reaction, ions with a positive electric charge produced at the oxidation side and ions with a negative electric charge produced at the reduction side need to move to the opposite sides. In an oxidation-reduction reaction in which $H_2O$ is used as an electron donor instead of a sacrificial catalyst, in particular, proton (hydrogen ion ($H^+$)) movement is indispensable.

A $CO_2$ dissolution technology that uses light energy and has a high photoreaction efficiency thus needs to be developed.

BRIEF DESCRIPTION OF THE DRAWING

FIG. 5 is a cross-sectional view showing a structure of a variation 1 of the photochemical reaction device of the first embodiment;

FIG. 6 is a cross-sectional view showing a structure of a variation 2 of the photochemical reaction device of the first embodiment;

FIG. 7 is a cross-sectional view showing a structure of a variation 3 of the photochemical reaction device of the first embodiment;

FIG. 8 is a cross-sectional view showing a structure of a variation 4 of the photochemical reaction device of the first embodiment;

FIGS. 9, 10, and 11 are plan views showing the structure of the photochemical reaction device of the first embodiment;

FIG. 12 is a table of an experimental result showing CO2 photoreduction efficiency in an example 1 in comparison with a comparative example;

FIG. 17 is a table of an experimental result showing CO2 photoreduction efficiency in an example 2 in comparison with the comparative example;

FIG. 18 is a table of an experimental result showing CO2 photoreduction efficiency in an example 3 comparison with the comparative example;

FIG. 19 is a plan view showing a structure of the photochemical reaction device in example 3;

FIG. 20 is a cross-sectional view showing the structure of the photochemical reaction device in example 3;

FIG. 35 is a block diagram showing a configuration of variation 4 of the photochemical reaction system of the configuration.

DETAILED DESCRIPTION

Figure 1:
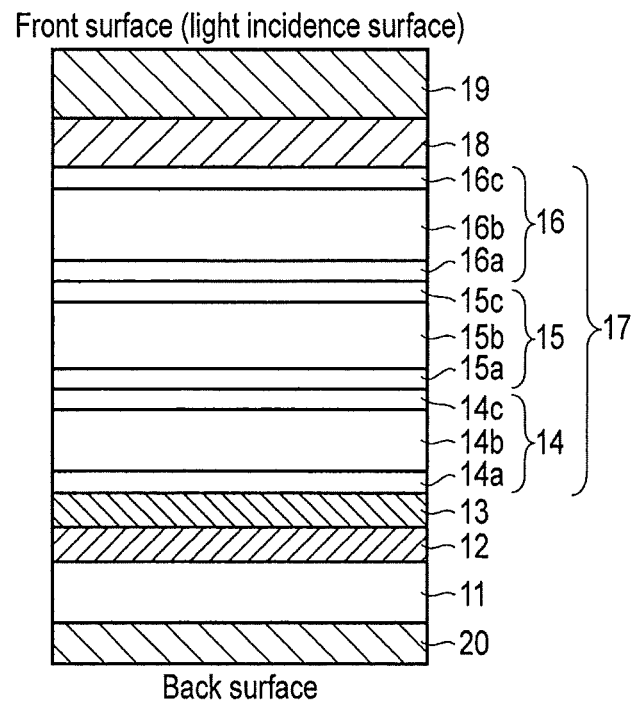
FIG. 1 is a cross-sectional view showing a structure of a photoelectrochemicalcell of an embodiment.

In general, according to one embodiment, a photochemical reaction system comprises a $CO_2$ production unit, a $CO_2$ absorption unit, and a $CO_2$ reduction unit. The $CO_2$ reduction unit comprises a laminated body and an ion transfer pathway. The laminated body comprises an oxidation catalyst layer producing $O_2$ and $H^+$ by oxidizing $H_2O$, a reduction catalyst layer producing carbon compounds by reducing $CO_2$ absorbed by the $CO_2$ absorption unit, and a semiconductor layer formed between the oxidation catalyst layer and the reduction catalyst layer and develops charge separation with light energy. The ion transfer pathway make ions move between the oxidation catalyst layer side and the reduction catalyst layer side. The oxidation catalyst layer oxidizes a reductant and the reduction catalyst layer reduces $CO_2$ by using an electron generated by oxidizing the reductant.

Referring to the accompanying drawings, an embodiment according to the present embodiment will be described. In the drawings, like numbers indicate like parts throughout the views. A repetitive description will be done as necessary.

1. Photoelectrochemicalcell

Figure 2:
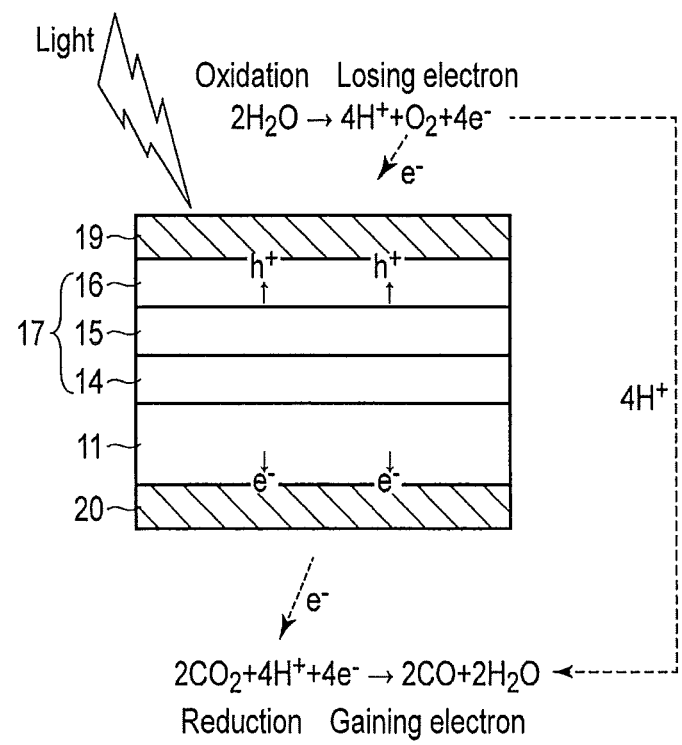
FIG. 2 is a cross-sectional view showing an operating principle of a photoelectrochemicalcell of the embodiment.

Referring to FIGS. 1 and 2, a photoelectrochemicalcell of the embodiment will be described below.

FIG. 1 is a cross-sectional view showing a structure of a photoelectrochemicalcell of the embodiment;

As shown in FIG. 1, the photoelectrochemicalcell of the embodiment has a laminated body including a substrate 11, a reflecting layer 12, a reduction electrode layer 13, a multi-junction photovoltaic cell 17, an oxidation electrode layer 18, an oxidation catalyst layer 19, and a reduction catalyst layer 20. On the front surface (light incidence surface) of the substrate 11, the reflecting layer 12, the reduction electrode layer 13, the multi-junction photovoltaic cell 17, the oxidation electrode layer 18, and the oxidation catalyst layer 19 are formed. On the back surface of the substrate 11, the reduction catalyst layer 20 is formed.

The substrate 11 is disposed for the purpose of supporting the photoelectrochemicalcell and increasing its mechanical strength. The substrate 11 has conductivity and is a metal plate made of a metal such as Cu, Al, Ti, Ni, Fe, and Ag, or an alloy plate including at least one of such metals, e.g. SUS. The substrate 11 can be made from conductive resin or the like. The substrate 11 can also be made of a semiconductor substrate such as Si, Ge, etc. As described later, the substrate 11 can be made of an ion exchange membrane.

The reflecting layer 12 is formed on a surface of the substrate 11. The reflecting layer 12 is made from a light reflective material such as a distributed Bragg reflecting layer including a metal layer or multi-layers of semiconductor materials. The reflecting layer 12, by being disposed between the substrate 11 and the multi-junction photovoltaic cell, makes light not absorbed by the multi-junction photovoltaic cell 17 to be reflected and enter the multi-junction photovoltaic cell 17 again. Because of this configuration, the light absorption rate of the multi-junction photovoltaic cell 17 can be improved.

The reduction electrode layer 13 is formed on the reflecting layer 12. The reduction electrode layer 13 is formed on an n-type semiconductor layer (n-type amorphous silicon layer 14a, which will be described later) of the multi-junction photovoltaic cell 17. Thus, it is desirable that the reduction electrode layer 13 is made from a material by which the reduction electrode layer is able to have ohmic contact with the n-type semiconductor layer. The reduction electrode layer 13 is made from a metal such as Ag, Au, Al, and Cu or an alloy including at least one of them. The reduction electrode layer 13 can also be made from a transparent conductive oxidation material such as ITO (Indium Tin Oxide), zinc oxide (ZnO), FTO (Fluorine doped Tin Oxide), AZO (Antimony doped Zinc Oxide), and ATO (Antimony doped Tin Oxide). The reduction electrode layer 13 may have a stacked structure of a metal and a transparent conductive oxidation material, a composite structure of a metal and another type of conductive material, or a composite structure of a transparent conductive oxidation material and another type of conductive material.

The multi-junction photovoltaic cell 17 is formed on the reduction electrode layer 13 and includes a first photovoltaic cell 14, a second photovoltaic cell 15, and a third photovoltaic cell 16. The first photovoltaic cell 14, the second photovoltaic cell 15, and the third photovoltaic cell 16 are photovoltaic cells which use a pin junction semiconductor and each cell has a different light absorption wavelength. With a layered structure of these photovoltaic cells, the multi-junction photovoltaic cell 17 is able to absorb solar light over a wide range of wavelengths and more efficient utilization of solar light energy becomes possible. A high open circuit voltage is also obtainable due to series connection of the photovoltaic cells.

More specifically, the first photovoltaic cell 14 includes an n-type amorphous silicon (a-Si) layer 14a, an intrinsic amorphous silicon germanium (a-SiGe) layer 14b, and a p-type microcrystal silicon (μc-Si) layer 14c, stacked from the bottom in this order. The a-SiGe layer 14b is a layer that absorbs light in a short wavelength range around 400 nm. That is, the first photovoltaic cell 14 develops charge separation with light energy in the short wavelength range.

The second photovoltaic cell 15 includes an n-type a-Si layer 15a, an intrinsic a-SiGe layer 15b, and a p-type μc-Si layer 15c, stacked from the bottom in this order. The a-SiGe layer 15b is a layer that absorbs light in a medium wavelength range of around 600 nm. That is, the second photovoltaic cell 15 develops charge separation with light energy in the medium wavelength range.

The third photovoltaic cell 16 includes an n-type a-Si layer 16a, an intrinsic a-SiGe layer 16b, and a p-type μc-Si layer 16c, stacked from the bottom in this order. The a-Si layer 16b is a layer that absorbs light in a long wavelength range of around 700 nm. That is, the third photovoltaic cell 16 develops charge separation with light energy in the long wavelength range.

As described above, the multi-junction photovoltaic cell 17 is able to develop charge separation with light of any wavelength. That is, holes move to a positive side (front surface side) and electrons move to a negative side (back surface side). This charge separation causes the multi-junction photovoltaic cell 17 to produce photovoltaic power.

Although the multi-junction photovoltaic cell 17 configured with a laminate structure of three photovoltaic cells is described above, the configuration of the multi-junction photovoltaic cell is not limited to this type. The multi-junction photovoltaic cell 17 may include a laminate structure of two or more than four photovoltaic cells. One photovoltaic cell can be used instead of the multi-junction photovoltaic cell 17. Although a photovoltaic cell using a pin junction semiconductor is described above, a photovoltaic cell using a pn (or pin) junction semiconductor can be used instead. Although the semiconductor layer is made from Si and Ge in the above example, the material is not limited to them; it can also be made from a compound semiconductor such as GaAs, GaInP, AlGaInP, CdTe, and CuInGaSe. Furthermore, a variety of forms such as a single crystal, a polycrystal, and an amorphous form can be applied.

The oxidation electrode layer 18 is formed on the multi-junction photovoltaic cell 17. The oxidation electrode layer 18 is formed on the p-type semiconductor layer (p-type μc-Si layer 16c) of the multi-junction photovoltaic cell 17. It is therefore desirable that the oxidation electrode layer 18 is made from a material which is able to have ohmic contact with the p-type semiconductor layer. The oxidation electrode layer 18 is made from a metal such as Ag, Au, Al, and Cu or an alloy including at least one of them. The oxidation electrode layer 18 can also be made from a transparent conductive oxidation material such as ITO, ZnO, FTO, AZO, and ATO. The oxidation electrode layer 18 may have a laminated structure of a metal and a transparent conductive oxidation material, a composite structure of a metal and another type of conductive material, or a composite structure of a transparent conductive oxidation material and another type of conductive material.

In this embodiment, irradiated light reaches the multi-junction photovoltaic cell 17 passing through the oxidation electrode layer 18. The oxidation electrode layer 18 disposed on the light-irradiation side therefore has a light transmission property for irradiated light. More specifically, the light transmission rate of the oxidation electrode layer 18 on the light-irradiation side needs to be at least 10% or more, more preferably 30% or more, of an amount of irradiated light.

The oxidation catalyst layer 19 is formed on the oxidation electrode layer 18. The oxidation catalyst layer 19 is formed on the positive side of the multi-junction photovoltaic cell 17 and produces $O_2$ and $H^+$ by oxidizing $H_2O$. The oxidation catalyst layer 19 is therefore made from a material which decreases the activation energy for oxidizing $H_2O$. In other words, the oxidation catalyst layer is made from a material which lowers the overvoltage when producing $O_2$ and $H^+$ by oxidizing $H_2O$. Such materials include binary metallic oxides such as Manganese oxide (Mn—O), Iridium oxide (Ir—O), Nickel oxide (Ni—O), Cobalt oxide (Co—O), Iron oxide (Fe—O), Tin oxide (Sn—O), Indium oxide (In—O), and Ruthenium oxide (Ru—O), ternary metallic oxides such as Ni—Co—O, La—Co—O, Ni—La—O, and Sr—Fe—O, quarternary metallic oxides such as Pb—Ru—Ir—O and La—Sr—Co—O, or a metal complex such as an Ru complex and an Fe complex. The configuration of the oxidation catalyst layer 19 is not limited to a film; the oxidation catalyst layer may be configured to be a grid, particulate, or wired structure.

In this embodiment, irradiated light reaches the multi-junction photovoltaic cell 17 passing through the oxidation catalyst layer 19 as well as the oxidation electrode layer 18. The oxidation catalyst layer 19 disposed on the light-irradiation side therefore has a light transmission property for irradiated light. More specifically, the light transmission rate of the oxidation catalyst layer 19 on the light-irradiation side needs to be at least 10% or more, more preferably 30% or more, of an amount of irradiated light.

The reduction catalyst layer 20 is formed on the back surface of the substrate 11. The reduction catalyst layer 20 is formed on the negative side of the multi-junction photovoltaic cell 17 and produces a carbon compound (e.g., carbon monoxide (CO), formic acid (HCOOH), methane ($CH_4$), methanol ($CH_3OH$), or ethanol ($C_2H_5OH$)) by reducing $CO_2$. The reduction catalyst layer 20 is therefore made from a material which decreases the activation energy for reducing $CO_2$. In other words, the reduction catalyst layer is made from a material which lowers the overvoltage when producing a carbon compound by reducing $CO_2$. Such materials include a metal such as Au, Ag, Cu, Pt, Ni, Zn, C, graphene, CNT (carbon nanotube), fullerene, Ketjen black, and Pd or an alloy including at least one of them or a metal complex such as an Ru complex and an Re complex. The configuration of the reduction catalyst layer 20 is not limited to a film; the reduction catalyst layer may be configured to be a grid, particulate, or wired structure.

The substrate 11 can be positioned on any of the positive side and negative side of the multi-junction photovoltaic cell 17. Although the oxidation catalyst layer 19 is disposed on the light incidence surface in this embodiment, the reduction catalyst layer 20 can be disposed on the light incidence surface. That is, in the photoelectrochemicalcell, the positions of the oxidation catalyst layer 19 and the reduction catalyst layer 20, the positions of the oxidation electrode layer 18 and the reduction electrode layer 13, and the polarities of the multi-junction photovoltaic cell are interchangeable. If such an interchange is applied, it is desirable that the reduction catalyst layer 20 and the reduction electrode layer 13 have transparency.

A protective layer may also be disposed on the front surface of the multi-junction photovoltaic cell 17 or between an electrode layer and a catalyst layer on the light-irradiation side (between the oxidation electrode layer 18 and the oxidation catalyst layer 19 in this embodiment). The protective layer has conductivity and prevents the multi-junction photovoltaic cell from corroding in an oxidation-reduction reaction as well. Such a feature of the protective layer extends the battery life of the multi-junction photovoltaic cell 17. The protective layer also has a light transmission property when needed. The protective layer can be a dielectric thin film such as $TiO_2$, $ZrO_2$, $Al_2O_3$, $SiO_2$, and $HfO_2$. The thickness needs to be desirably 10 nm or less, more preferably 5 nm or less, to have conductivity via the tunnel effect.

FIG. 2 is a cross-sectional view showing an operating principle of the photoelectrochemicalcell of the embodiment. In FIG. 2, the reflecting layer 12, the reduction electrode layer 13, and the oxidation electrode layer 18 are not shown.

As shown in FIG. 2, light entering on the front side passes through the oxidation catalyst layer 19 and the oxidation electrode layer 18 and reaches the multi-junction photovoltaic cell 17. The multi-junction photovoltaic cell 17, if it absorbs light, produces photoexcited electrons and their pairing holes and separates them. That is, in each photovoltaic cell (the first photovoltaic cell 14, the second photovoltaic cell 15, and the third photovoltaic cell 16), charge separation in which photoexcited electrons move to the n-type semiconductor layer side (the side facing the reduction catalyst layer 20) and holes pairing with the photoexcited electrons move to the p-type semiconductor layer (the side facing the oxidation catalyst layer 19) takes place. This charge separation causes the multi-junction photovoltaic cell 17 to produce photovoltaic power.

As described above, photoexcited electrons created inside the multi-junction photovoltaic cell 17 are used for the reduction reaction in the reduction catalyst layer 20, which is an anode, and holes are used for the oxidation reaction in the oxidation catalyst layer 19, which is a cathode. Accordingly, a reaction according to the formula (1) takes place in the vicinity of the oxidation catalyst layer 19 and a reaction according to the formula (2) takes place in the vicinity of the reduction catalyst layer 20.

$$2H_2O \rightarrow 4H^+ + O_2 + 4e^- \quad (1)$$

$$2CO_2 + 4H^+ + 4e^- \rightarrow 2CO + 2H_2O \quad (2)$$

As shown in the formula (1), $H_2O$ is oxidized (losing an electron) and $O_2$ and $H^+$ are produced in the vicinity of the oxidation catalyst layer 19. $H^+$ produced on the side where the oxidation catalyst layer 19 exists moves to the side where the reduction catalyst layer 20 exists through an ion transfer pathway, which will be described later.

As shown in the formula (2), in the vicinity of the reduction catalyst layer 20, a reaction between $CO_2$ and $H^+$, which has moved there, takes place and carbon monoxide (CO) and $H_2O$ are produced. That is, $CO_2$ is reduced (attaining an electron).

In this process, the multi-junction photovoltaic cell 17 need to have an open circuit voltage equal to or higher than the potential difference between the standard oxidation reduction potential of an oxidation reaction taking place in the oxidation catalyst layer 19 and the standard oxidation reduction potential of a reduction reaction taking place in the reduction catalyst layer 20. For example, the standard oxidation reduction potential of the oxidation reaction in the formula (1) is 1.23 [V] and the standard oxidation reduction potential of the reduction reaction in the formula (2) is −0.1 [V]. The open circuit voltage of the multi-junction photovoltaic cell 17 thus needs to be equal to or higher than 1.33 [V]. More preferably, the open circuit voltage needs to be equal to or higher than the potential difference including the overvoltage. More specifically, in the case that the overvoltage in an oxidation reaction according to the formula (1) and the overvoltage in a reduction reaction according to the formula (2) are both 0.2 [V], the open circuit voltage needs to be equal to or higher than 1.73 [V].

Not only the reduction reaction from $CO_2$ to CO shown in the formula (2) but also a reduction reaction from $CO_2$ to HCOOH, $CH_4$, $CH_3OH$, $C_2H_5OH$, or the like is a reaction that consumes $H^+$. If $H^+$ produced in the oxidation catalyst layer 19 cannot move to the reduction catalyst layer 20 at the opposite end, the overall reaction performance therefore becomes lower. In response to this, in this embodiment, a high reaction performance can be achieved through improvement in $H^+$ transfer by forming an ion transfer pathway through which $H^+$ moves.

2. Photochemical Reaction Device

Referring to FIGS. 3 to 23, a photochemical reaction device using a photoelectrochemicalcell of the embodiment will be described below.

2-1. First Embodiment

Referring to FIGS. 3 to 12, a photochemical reaction device of a first embodiment will be described below.

A photochemical reaction device of the first embodiment has a photoelectrochemicalcell configured in a laminated body of an oxidation catalyst layer 19, a reduction catalyst layer 20, and a multi-junction photovoltaic cell 17 disposed therebetween and an ion transfer pathway through which ions move between the oxidation catalyst layer 19 and the reduction catalyst layer 20. Due to this structure, $H^+$ produced on the side where the oxidation catalyst layer 19 exists can be moved to the reduction catalyst layer 20 with high photoreaction efficiency and carbon dioxide can be dissolved on the side where the reduction catalyst layer 20 exists by this H. The first embodiment will be described in detail below.

Structure of First Embodiment

A structure of the photochemical reaction device of the first embodiment will be described first below.

Figure 3:
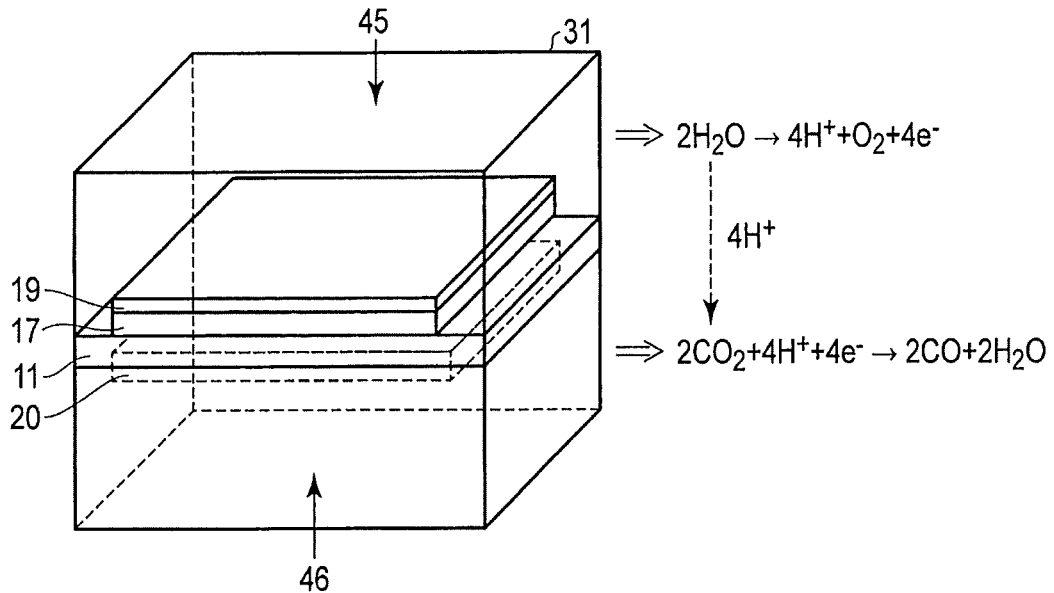
FIG. 3 is a perspective view showing a structure of a photochemical reaction device of a first embodiment.
Figure 4:
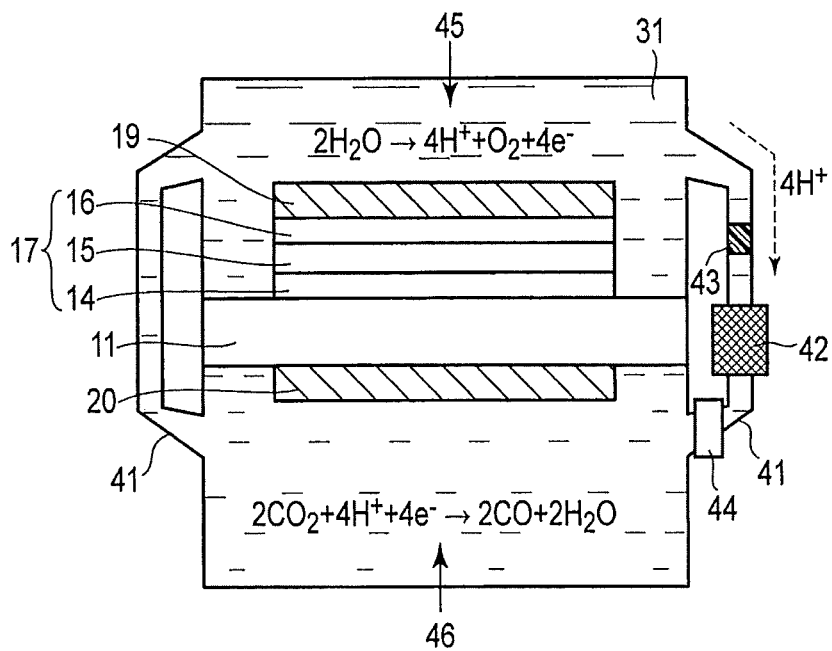
FIG. 4 is a cross-sectional view showing the structure of the photochemical reaction device of the first embodiment.

FIG. 3 is a perspective view showing a structure of the photochemical reaction device of the first embodiment. FIG. 4 is a cross-sectional view showing the structure of the photochemical reaction device of the first embodiment. In FIG. 3, an ion transfer pathway, which will be described later, is not shown.

As shown in FIGS. 3 and 4, the photochemical reaction device of the first embodiment has a photoelectrochemicalcell, an electrolytic tank 31 including the photoelectrochemicalcell therein, and an electrolytic tank flow path 41 connected to the electrolytic tank 31 and used as an ion transfer pathway.

The photoelectrochemicalcell is formed in flat layers and divides the electrolytic tank 31 into at least two parts with the substrate 11. That is, the electrolytic tank 31 has an oxidation reaction electrolytic tank 45, to which the oxidation catalyst layer 19 of the photoelectrochemicalcell is disposed, and a reduction reaction electrolytic tank 46, to which the reduction catalyst layer 20 of the photoelectrochemicalcell is disposed. The oxidation reaction electrolytic tank 45 and the reduction reaction electrolytic tank 46 can be provided with different electrolytic solutions.

The oxidation reaction electrolytic tank 45 is filled with an electrolytic solution, e.g., a liquid including $H_2O$. While such an electrolytic solution may include any electrolyte, it is desirable that an electrolytic solution which advances the oxidation reaction of $H_2O$ is chosen. In the oxidation reaction electrolytic tank 45, O2 and $H^+$ are produced through the oxidation of $H_2O$ by the oxidation catalyst layer 19.

The reduction reaction electrolytic tank 46 is filled with an electrolytic solution, e.g., a liquid including $CO_2$. It is desirable that the electrolytic solution in the reduction reaction electrolytic tank 46 reduces the reduction potential of $CO_2$, has high ion conductivity, and has a $CO_2$ absorbent for absorbing $CO_2$. Such an electrolytic solution includes an ionic liquid, which is made of salt of a cation such as an imidazolium ion or a pyridinium ion and an anion such as $BF_4^-$ and $PF_6^-$ and is in a liquid state in a wide temperature range, or its aqueous solution. An amine solution such as ethanoleamine, imidazole, and pyridine or its aqueous solution can also be used as an electrolytic solution. Any of a primary amine, secondary amine, or tertiary amine can be used. A primary amine may be a methylamine, ethylamine, propylamine, butylamine, pentylamine, and hexylamine. A hydrocarbon in an amine can be replaced with an alcohol, halogen, or the like. An amine the hydrocarbon of which is replaced includes, for example, a methanolamine, ethanolamine, chloromethylamine, etc. An unsaturated bond may exist for an amine. The replacement of hydrocarbons applies to a secondary amine and a tertiary amine as well. A secondary amine includes a dimethylamine, diethylamine, dipropylamine, dipentylamine, dihexylamine, dimethanolamine, diethanolamine, and dipropanolamine. Different substances may replace hydrocarbons. This also applies to a tertiary amine. An amine with different replacements may be, for example, a methylethylamine, methylpropylamine, etc. A tertiary amine may be a trimethylamine, triethylamine, tripropylamine, tributylamine, trihexylamine, trimethanolamine, triethanolamine, tripropanolamine, tributanolamine, tripropanolamine, trihexanolamine, methyldiethylamine, methyldipropylamine, etc. A cation in ionic liquid may be a 1-ethyl-3-methylimidazolium ion, 1-methyl-3-propylimidazolium ion, 1-butyl-3-methylimidazole ion, 1-methyl-3-pentylimidazolium ion, 1-hexyl-3-methylimidazolium ion, etc. Position 2 of an imidazolium ion may be replaced by another substance. For example, such an imidazolium ion may be a 1-ethyl-2,3-dimethylimidazolium ion, 1,2-dimethyl-3-propylimidazolium ion, 1-butyl-2,3-dimethylimidazolium ion, 1,2-dimethyl-3-pentylimidazolium ion, 1-hexyl-2,3-dimethylimidazolium ion, etc. A pyridinium ion may be a methylpyridinium, ethylpyridinium, propylpyridinium, butylpyridinium, pentylpyridinium, hexylpyridinium, etc. For both the imidazolium ion and pyridinium ion, an alkyl group may be replaced by another substance and an unsaturated bond may exist. An anion may be a fluoride ion, chloride ion, bromide ion, iodide ion, $BF_4^-$, $PF_6^-$, $CF_3COO^-$, $CF_3SO_3^-$, $NO_3^-$, $SCN^-$, $(CF_3SO_2)_3C^-$, bis(trifluoromethoxysulfonyl)imide, bis(trifluoromethoxysulfonyl)imide, bis(perfluoroethylsulfonyl) imide, etc. A dipolar ion that is made by combining a cation and an anion in an ionic liquid with a hydrocarbon may be used as well. In the reduction reaction electrolytic tank 46, carbon compounds are produced through the reduction of $CO_2$ by the reduction reaction layer 20.

Temperatures of the electrolytic solutions filling the oxidation reaction electrolytic tank 45 and the reduction reaction electrolytic tank 46 may take the same value or different values depending on their usage environment. If the electrolytic solution used for the reduction reaction electrolytic tank 46 is an amine absorbing solution which includes $CO_2$ emitted from a factory, for example, the temperature of the electrolytic solution is higher than the atmospheric atmosphere temperature. In this case, the electrolytic solution temperature needs to be 30° C. or higher and 150° C. or lower, more preferably 40° C. or higher and 120° C. or lower.

The electrolytic tank flow path 41 is disposed, for example, beside the electrolytic tank 31. One end of the electrolytic tank flow path 41 is connected to the oxidation reaction electrolytic tank 45 and the other end is connected to the reduction reaction electrolytic tank 46. That is, the electrolytic tank flow path 41 connects the oxidation reaction electrolytic tank 45 with the reduction reaction electrolytic tank 46.

An ion exchange membrane 43 is disposed in a portion of the electrolytic tank flow path 41 and allows a particular type of ion to pass through. By this structure, the electrolytic solution of the oxidation reaction electrolytic tank 45 can be separated from the electrolytic solution of the reduction reaction electrolytic tank 46, and only a particular type of ion can be moved through the electrolytic tank flow path 41 equipped with the ion exchange membrane 43. That is, the photochemical reaction device has a diaphragm structure that selectively allows substances to pass through. The ion exchange membrane 43 in the above structure is a proton exchange membrane and is able to make $H^+$ produced in the oxidation reaction electrolytic tank 45 move to the reduction reaction electrolytic tank 46. More specifically, the types of the ion exchange membrane 43 include a cation exchange membrane such as Nafion and Flemion and an anion exchange membrane such as Neosepta and Selemion.

Another substance that can make ions move and separate electrolytic solutions, e.g., an agar such as salt bridge, can be used instead of the ion exchange membrane 43. By using a solid polymer membrane, which has proton exchangeability and is represented by Nafion, in general, a high ion movability can be attained.

The electrolytic tank flow path 41 may be equipped with a circulation mechanism 42 such as a pump. With the mechanism, ion ($H^+$) circulation between the oxidation reaction electrolytic tank 45 and the reduction reaction electrolytic tank 46 can be improved. Two electrolytic tank flow paths 41 may be disposed and, by using the circulation mechanism 42 attached to at least one of these electrolytic tank flow paths, ions may be moved from the oxidation reaction electrolytic tank 45 to the reduction reaction electrolytic tank 46 via one of the electrolytic tank flow paths 41 and from the reduction reaction electrolytic tank 46 to the oxidation reaction electrolytic tank 45 via the other electrolytic tank flow path 41. A plurality of circulation mechanisms 42 may also be attached. In order to reduce diffusion of ions and circulate ions with higher efficiency, a plurality (three or more) of electrolytic tank flow paths 41 may be arranged. Making the liquid flow smoothly may also cause bubbles of created gas not to stay on a surface of the electrode and electrolytic layer and thus reduction in efficiency or light amount distribution caused by sunlight scattering due to the bubbles to be controlled.

Producing a temperature difference between the electrolytic liquids using raised heat by radiating light on a surface of the multi-junction photovoltaic cell 17 may make ion diffusion decrease and ions circulate with improved efficiency. In other words, ion movement can be accelerated by convection other than ion diffusion.

Photovoltaic cell performance and catalyst performance can be controlled by disposing a temperature adjustment mechanism 44, which executes temperature control for electrolytic solutions, in the electrolytic tank flow path 41 and electrolytic tank 31 and executing temperature control with the mechanism. This arrangement can, for example, homogenize a temperature of the reaction system in order to stabilize and improve the performance of the photovoltaic cell and catalyst. Temperature rise can also be prevented for system stabilization. Temperature control may alter the selectivity of the photovoltaic cell and catalyst and also control materials from them.

In this embodiment, an edge of the substrate 11 projects out over edges of the multi-junction photovoltaic cell 17, the oxidation reaction layer 19, and the reduction reaction layer 20. However, the arrangement is not limited to this. The substrate 11, the multi-junction photovoltaic cell 17, the oxidation reaction layer 19, and the reduction reaction layer 20 may be flat plates with the same area.

Variations of First Embodiment

Next, a variation of the photochemical reaction device of the first embodiment will be described below.

FIGS. 5 to 8 are cross-sectional views showing structures of variations 1 to 4 of the photochemical reaction device of the first embodiment. Only differences from the above-described structure of the photochemical reaction device of the first embodiment will be described.

As shown in FIG. 5, the variation 1 of the photochemical reaction device of the first embodiment has a photoelectrochemicalcell, an electrolytic tank 31 which includes the photoelectrochemicalcell, and an opening 51 which is formed in a substrate 11 as an ion transfer pathway.

The opening 51 is, for example, formed so as to penetrate the substrate 11 at its edge from the side facing the oxidation reaction electrolytic tank 45 to the side facing the reduction reaction electrolytic tank 46. With this arrangement, the opening 51 connects the oxidation reaction electrolytic tank 45 with the reduction reaction electrolytic tank 46.

A portion of the opening 51 is filled with an ion exchange membrane 43, which makes particular ions pass through. This arrangement makes it possible to separate the electrolytic solution in the oxidation reaction electrolytic tank 45 from the electrolytic solution in the reduction reaction electrolytic tank 46 and, at the same time, to make particular ions move via the opening 51 filled with the ion exchange membrane 43.

As shown in FIG. 6, variation 2 of the photovoltaic reaction device of the first embodiment has a photoelectrochemicalcell, an electrolytic tank 31 which includes the photoelectrochemicalcell, and an opening 51 formed in a substrate 11, a multi-junction photovoltaic cell 17, an oxidation catalyst layer 19, and a reduction catalyst layer 20 as an ion transfer pathway.

The opening 51 is formed so as to penetrate the substrate 11, the multi-junction photovoltaic cell 17, the oxidation catalyst layer 19, and the reduction catalyst layer 20 from the side facing the oxidation reaction electrolytic tank 45 to the side facing the reduction reaction electrolytic tank 46. With this arrangement, the opening 51 connects the oxidation reaction electrolytic tank 45 with the reduction reaction electrolytic tank 46.

A portion of the opening 51 is filled with an ion exchange membrane 43, which makes particular ions pass through. This arrangement makes it possible to separate the electrolytic solution in the oxidation reaction electrolytic tank 45 from the electrolytic solution in the reduction reaction electrolytic tank 46 and, at the same time, to make particular ions move via the opening 51 filled with the ion exchange membrane 43.

Although in FIG. 6, the ion exchange membrane 43 is disposed at a portion of the opening 51, the ion exchange membrane 43 may be formed so as to fill up the inside of the opening 51.

As shown in FIG. 7, variation 3 of the photovoltaic reaction device of the first embodiment has a photoelectrochemicalcell, an electrolytic tank 31 which includes the photoelectrochemicalcell, and an opening 51 formed in a substrate 11, a multi-junction photovoltaic cell 17, an oxidation catalyst layer 19, and a reduction catalyst layer 20 as an ion transfer pathway.

The opening 51 is formed so as to penetrate the substrate 11, the multi-junction photovoltaic cell 17, the oxidation catalyst layer 19, and the reduction catalyst layer 20 from the side facing the oxidation reaction electrolytic tank 45 to the side facing the reduction reaction electrolytic tank 46. With this arrangement, the opening 51 connects the oxidation reaction electrolytic tank 45 with the reduction reaction electrolytic tank 46.

The ion exchange membrane 43 is disposed so as to cover the light-irradiation surface (front surface of the oxidation catalyst layer 19) of the photoelectrochemicalcell. Due to this arrangement, the end of the opening 51 facing the oxidation reaction electrolytic tank 45 is covered with the ion exchange membrane 43. The ion exchange membrane 43 allows only particular ions to pass through. This arrangement makes it possible to separate the electrolytic solution in the oxidation reaction electrolytic tank 45 from the electrolytic solution in the reduction reaction electrolytic tank 46 and, at the same time, to make particular ions move via the opening 51 filled with the ion exchange membrane 43.

Moreover, in the variation 3, a surface of the oxidation catalyst layer 19 is covered with the ion exchange membrane 43. Due to this arrangement, the ion exchange membrane 43 performs a role of a protective layer for the oxidation catalyst layer 19 and the multi-junction photovoltaic cell 17 as well.

As shown in FIG. 8, variation 4 of the photovoltaic reaction device of the first embodiment has a photoelectrochemicalcell, an electrolytic tank 31 which includes the photoelectrochemicalcell, and an opening 51 formed in a multi-junction photovoltaic cell 17, an oxidation catalyst layer 19, and a reduction catalyst layer 20 as an ion transfer pathway.

In the variation 4, an ion exchange membrane 43 is disposed as a replacement of a substrate 11. That is, the multi-junction photovoltaic cell 17 and the oxidation catalyst layer 19 are disposed on the front surface and the reduction catalyst layer 20 is disposed on the back surface of the ion exchange membrane 43.

The opening 51 is formed so as to penetrate the multi-junction photovoltaic cell 17 and the oxidation catalyst layer 19 from the side facing the oxidation reaction electrolytic tank 45 to the side facing the reduction reaction electrolytic tank 46, and also to penetrate the reduction catalyst layer 20 from the side facing the oxidation reaction electrolytic tank 45 to the side facing the reduction reaction electrolytic tank 46. This arrangement configures a structure in which the ion exchange membrane 43 is disposed inside the opening 51. In other words, the side facing the oxidation reaction electrolytic tank 45 is separated from the side facing the reduction reaction electrolytic tank 46 with just the ion exchange membrane 43.

The ion exchange membrane 43 allows only particular ions to pass through. This arrangement makes it possible to separate the electrolytic solution in the oxidation reaction electrolytic tank 45 from the electrolytic solution in the reduction reaction electrolytic tank 46 and, at the same time, to make particular ions move via the opening 51 filled with the ion exchange membrane 43. Moreover, ions can be moved through not only the opening 51 but also projecting-out edges of the ion exchange membrane 43.

Figure 9:
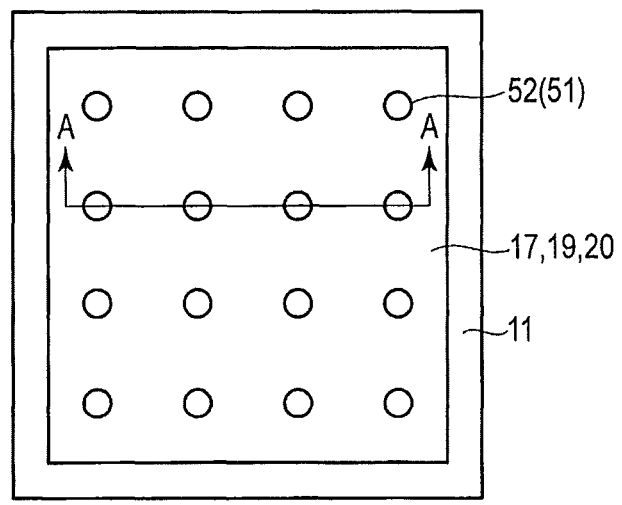
Figure 10:
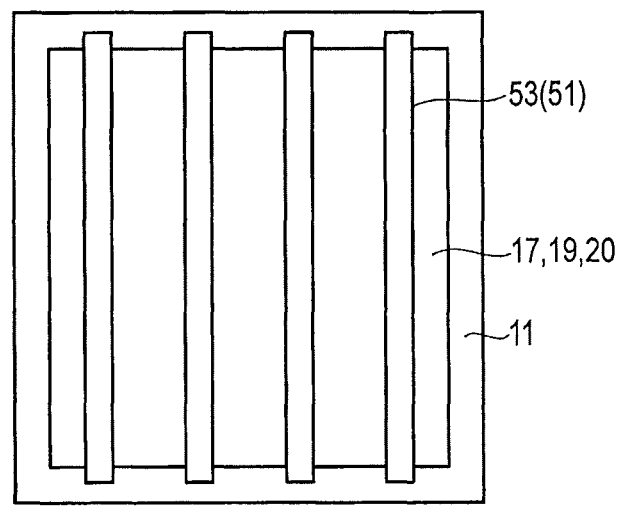

FIGS. 9 to 11 are plan views showing the structure of the photochemical reaction device of the first embodiment and mainly illustrate examples of the planar shape of the opening 51.

As shown in FIG. 9, the opening 51 is formed as, for example, a through-hole 52 which penetrates the substrate 11, the multi-junction photovoltaic cell 17, the oxidation catalyst layer 19, and the reduction catalyst layer 20 and the planar shape of the opening is circular. A plurality of through-holes 52 may be formed in the embodiment. The plurality of through-holes 52 are arranged in a square lattice along a first axis and a second axis orthogonal to the first axis.

The lower limit for the diameter (equivalent circle diameter) of the through-holes 52, which allows $H^+$ to move therethrough, is preferably 0.3 nm or larger. The equivalent circle diameter above is defined as $((4 \times area)/\pi) \times 0.5$.

The planar shape of the through-hole 52 is not limited to a circular shape. It may be elliptical, triangular, or square. The arrangement of the plurality of through-holes 52 is not limited to a square lattice and may be a triangular lattice or random lattice. The through-hole 52 just needs to have a continuous opening from the oxidation catalyst layer 19 to the reduction catalyst layer 20 except the ion exchange membrane 43 and need not have the same diameter throughout the layers. The diameter of the through-hole 52 from the oxidation catalyst layer 19 to the multi-junction photovoltaic cell 17 may differ from the diameter of the through-hole 52 from the reduction catalyst layer 20 to the multi-junction photovoltaic cell 17. Even if a burr or roughness emerges on the side wall of the through-hole 52 in a manufacturing process, its effectiveness does not change.

As shown in FIG. 10, the opening 51 is formed as, for example, a slit 53 which penetrates the substrate 11, the multi-junction photovoltaic cell 17, the oxidation catalyst layer 19, and the reduction catalyst layer 20 and the planar shape of the opening is rectangular. A plurality of slits 53 may be formed in this embodiment. The plurality of slits 53 may extend along a first direction and be arranged in a row along a second direction.

The lower limit for the width (shortest width) of the slits 53, which allows $H^+$ to move therethrough, is preferably 0.3 nm or larger.

As shown in FIG. 11, the opening 51 is formed as, for example, a slit 54 which isolates the substrate 11, the multi-junction photovoltaic cell 17, the oxidation catalyst layer 19, and the reduction catalyst layer 20 and the planar shape of the opening is rectangular. That is, a plurality of laminated bodies each of which includes the substrate 11, the multi-junction photovoltaic cell 17, the oxidation catalyst layer 19, and the reduction catalyst layer 20 are formed and the slits 54 are disposed among the plurality of laminated bodies. The plurality of laminated bodies are supported by not-shown frames or the like. A plurality of slits 54 may be formed in this embodiment. The plurality of slits 54 may extend along a first direction in parallel and be arranged in a row along a second direction.

Manufacturing Method of First Embodiment

Next, a manufacturing method of the photochemical reaction device of the first embodiment will be described below. A case in which a through-hole 52 is formed as an opening 51 used as an ion transfer pathway is described below.

First, a structure including the substrate 11, the reflecting layer 12, the reduction electrode layer 13, the multi-junction photovoltaic cell 17, and the oxidation electrode layer 18 is prepared. The reflecting layer 12, the reduction electrode layer 13, the multi-junction photovoltaic cell 17, and the oxidation electrode layer 18 are formed on the front surface of the substrate 11 in this order. A multi-junction photovoltaic cell 17, which is composed of a first photovoltaic cell 14, a second photovoltaic cell 15, and a third photovoltaic cell 16, made of a pin junction semiconductor, is used for a photovoltaic cell.

Next, the oxidation catalyst layer 19 is formed on the oxidation electrode layer 18 by a sputtering method or coating method. The oxidation catalyst layer 19 is made from, for example, a binary metallic oxide such as Manganese oxide (Mn—O), Iridium oxide (Ir—O), Nickel oxide (Ni—O), Cobalt oxide (Co—O), Iron oxide (Fe—O), and Ruthenium oxide (Ru—O), a ternary metallic oxide such as Ni—Co—O, La—Co—O, Ni—La—O, and Sr—Fe—O, a quarternary metallic oxide such as Pb—Ru—Ir—O and La—Sr—Co—O, or a metal complex such as an Ru complex and an Fe complex. The configuration of the oxidation catalyst layer 19 is not limited to a film; the oxidation catalyst layer may be configured to be a grid, particulate, or wired structure.

On the back surface of the substrate 11, the reduction catalyst layer 20 is formed with, for example, a vacuum evaporation method, sputtering method, or coating method. The reduction catalyst layer 20 is made from, for example, a metal such as Au, Ag, Cu, Pt, C, Ni, Zn, graphen, CNT, fullerene, Ketjen black, and Pd or an alloy including at least one of them or a metal complex such as an Ru complex and an Re complex. The configuration of the reduction catalyst layer 20 is not limited to a film; the reduction catalyst layer may be configured to be a grid, particulate, or wired structure.

A photoelectrochemicalcell made of a laminated body of the substrate 11, the reflecting layer 12, the reduction electrode layer 13, the multi-junction photovoltaic cell 17, the oxidation electrode layer 18, the oxidation catalyst layer 19, and the reduction catalyst layer 20 is thus formed.

Next, a through-hole 52 which penetrates the photoelectrochemicalcell from the oxidation catalyst layer 19 to the reduction catalyst layer 20 is formed.

One of the methods to form the through-hole 52 is, for example, etching after forming a mask pattern. More specifically, after forming a mask pattern on the oxidation catalyst layer 19 (on the front surface) or the reduction catalyst layer 20 (on the back surface), the substrate 11, the reflecting layer 12, the reduction electrode layer 13, the multi-junction photovoltaic cell 17, the oxidation electrode layer 18, the oxidation catalyst layer 19, and the reduction catalyst layer 20 are etched using the mask pattern.

The methods to form a mask pattern include a method by a widespread optical lithography or an electron beam lithography. A method using imprint technology or a method using a block copolymer or molecular self-assembly pattern can be used as well. The methods of etching include a dry etching method using a reactive gas such as a chlorine-based gas or a wet etching method using an acid solution or an alkaline solution. A direct processing method such as laser beam machining, press working, and cutting is useful in the sense that it has an advantage in the small number of process steps.

The through-hole 52 is thus formed in the substrate 11, the reflecting layer 12, the reduction electrode layer 13, the multi-junction photovoltaic cell 17, the oxidation electrode layer 18, the oxidation catalyst layer 19, and the reduction catalyst layer 20. Next, disposing the photoelectrochemical-cell to which the through-hole 52 is formed in the electrolytic tank 31 completes an assembly of the photochemical reaction device.

Effect of First Embodiment

According to the first embodiment described above, the photochemical reaction device has a photoelectrochemical-cell configured in a laminated body of the oxidation catalyst layer 19, the reduction catalyst layer 20, and the multi-junction photovoltaic cell 17 disposed therebetween and the ion transfer pathway through which ions ($H^+$) are moved between the oxidation catalyst layer 19 and the reduction catalyst layer 20. With this configuration, $H^+$ produced in the oxidation catalyst layer 19 can be transferred to the reduction catalyst layer 20 through the ion transfer pathway. As a result, a high photoreduction efficiency can be achieved by accelerating a reductive decomposition of $CO_2$ in the reduction catalyst layer 20.

The energy (potential) necessary for the oxidation of $H_2O$ in the vicinity of the oxidation catalyst layer 19 and the reduction of $CO_2$ in the vicinity of the reduction catalyst layer 20 is provided by the photovoltaic power produced in the multi-junction photovoltaic cell 17. To let light enter, a transparent electrode is generally used for an electrode which is provided in order to collect photoexcited electrons produced in charge separation in the photovoltaic cell of the comparative example. However, because a transparent electrode has a high resistance, the efficiency in collecting electricity may be reduced. Thus, metal wirings which have no transparency are connected to the transparent electrode as an auxiliary electrode in some cases. In that case, however, because irradiance decreases due to cutting-off of incoming light by the metal wirings, the efficiency is further reduced. Furthermore, because the metal wirings are usually formed in long and slim shapes, the resistance of the electrode in collecting electricity (electrons) via the metal wirings increases.

In the first embodiment, the oxidation catalyst layer 19 and the reduction catalyst layer 20, both being flat plate-shaped, are disposed on the front surface and the back surface of the multi-junction photovoltaic cell 17, respectively. Due to this arrangement, an oxidation-reduction reaction takes place by the catalysts instantly after the multi-junction photovoltaic cell 17 produces charge separation. In other words, charge separation takes place at the multi-junction photovoltaic cell 17 and an oxidation-reduction reaction takes place at the oxidation catalyst layer 19 and the reduction catalyst layer 20. Due to this arrangement, photovoltaic power produced by the multi-junction photovoltaic cell 17 can efficiently be applied to the oxidation catalyst layer 19 and the reduction catalyst layer 20 without increasing the resistance caused by metal wirings. Simplification of a structure can also be achieved because forming metal wirings or the like is not necessary.

In a case in which electricity is collected from the photovoltaic cell via metal wirings in the comparative example, the complexity of a structure leads to areas being enlarged. Thus, the area of an electrode needs to be reduced in order to secure a small size. As a result, reaction with high current density is necessary. In this case, because a high performance catalyst that can accelerate a reaction with high current density is limited, a precious metal is often used.

In the first embodiment, the area of a portion other than the electrode is not necessary because of a laminate structure of the multi-junction photovoltaic cell 17, the oxidation catalyst layer 19, and the reduction catalyst layer 20. Thus, both a small size and an enlarged electrode area can be achieved simultaneously and reaction with a relatively low current density is possible. With this configuration, a general purpose metal can be used due to a wide range of alternatives for a catalytic metal. It is also easy to secure reaction selectivity.

The $CO_2$ photoreduction efficiency for a case in which the through-hole 52 is formed as an ion transfer pathway in the first embodiment will be described below.

FIG. 12 is a table of an experimental result showing $CO_2$ photoreduction efficiency in example 1 in comparison with a comparative example. More specifically, the table shows $CO_2$ photoreduction efficiencies for example 1 (1-1 to 1-12), all in relative values scaled to the $CO_2$ photoreduction efficiency for the comparative example, which is assumed to be 1.00. Details of FIG. 12 will be described below.

Example 1 is an example of the photoelectrochemicalcell in the photochemical reaction device of the first embodiment. More specifically, the photoelectrochemicalcell of example 1 has the through-hole 52 through which only $H^+$ can be moved and the equivalent circle diameter of which is relatively large. In example 1, twelve photoelectrochemicalcells (sample cell numbers 1-1 to 1-12), the through-holes 52 of which have equivalent circle diameters of 50, 100, and 200 µm and area ratios of 10, 20, 30, and 40%, were produced and their $CO_2$ photoreduction efficiencies were evaluated. These photoelectrochemicalcells in example 1 were produced as described below.

First, a structure that has the multi-junction photovoltaic cell 17 including a pin-type a-Si layer, a-SiGe layer, and a-SiGe layer, the oxidation electrode layer 18 made from ITO and formed on the front surface of the multi-junction photovoltaic cell 17, the reduction electrode layer 13 made from ZnO and formed on the front surface of the multi-junction photovoltaic cell 17, the reflecting layer 12 made from Ag and formed on the back surface of the reduction electrode layer 13, and the SUS substrate 11 formed on the back surface of the reflecting layer 12 is prepared. In this configuration, the thickness of the multi-junction photovoltaic cell 17 is 500 nm, the thickness of the oxidation electrode layer 18 is 100 nm, the thickness of the reduction electrode layer 13 is 300 nm, the thickness of the reflecting layer 12 is 200 nm, and the thickness of the SUS substrate is 1.5 mm. The oxidation catalyst layer 19 is disposed on the p-type surface of the multi-junction semiconductor and the reduction catalyst layer 20 is disposed on the n-type surface of the multi-junction semiconductor.

Next, the oxidation catalyst layer 19 made from $Co_3O_4$ is formed on the front surface of the oxidation electrode layer 18 by a sputtering method. On the back surface of the SUS substrate 11, the reduction catalyst layer 20 made from Au is formed with a vacuum evaporation method. In this process, the thickness of the oxidation catalyst layer 19 is 100 nm and the thickness of the reduction catalyst layer 20 is 100 nm.

A laminated body (cell) of the substrate 11, the reflecting layer 12, the reduction electrode layer 13, the multi-junction photovoltaic cell 17, the oxidation electrode layer 18, the oxidation catalyst layer 19, and the reduction catalyst layer 20 is thus formed. Next, light is irradiated on the laminated body from the side facing the oxidation catalyst layer 19 by a solar simulator (AM1.5, 1000 W/m$^2$) and the open circuit voltage of the cell at the irradiation is measured. Based on the measurement, the open circuit voltage of the cell is set to 1.9 [V].

Next, the through-hole 52 is formed in the cell. The through-hole 52 is formed by irradiating a laser beam on the prepared cell. Laser beam irradiation parameters are as follows: wavelength of 515 nm; pulse width of 15 ps; and repetition frequency of 82 MHz. The laser beam is concentrated with an object lens of 10-fold magnification and irradiated on the cell. With this process, a plurality of through-holes 52 in an arrangement of a triangular lattice is formed in the cell. Next, each through-hole 52 is trimmed using a laser beam again so as to be perpendicular.

Next, the cell to which the through-hole 52 is formed is cut into a square shape and the edges of the cell are sealed with epoxy resin so that the area of the exposed part is 1 cm$^2$. Then, an image of the cell is taken with an optical microscope or scanning electron microscope from an angle of view such that about one hundred through-holes 52 are captured and the equivalent circle diameter and area ratio of the through-hole 52 of each cell are measured with image processing software. By the above process, the photoelectrochemicalcells (sample cell numbers 1-1 to 1-12) of example 1 were produced.

In contrast, the photoelectrochemicalcell of the comparative example is a photoelectrochemicalcell that has no through-hole 52 and has the same structure as the cell of example 1 except the through-hole 52.

The CO$_2$ photoreduction efficiency was measured by a method to be described below. First, the cell was dipped in a closed-system tank (electrolytic tank 31) which contained a solution of 0.1 M (mol/l) KHCO$_3$ produced by bubbling CO$_2$ gas for ten minutes. Next, light was irradiated on the cell from the side where the oxidation catalyst layer 19 exists by a solar simulator (AM1.5, 1000 W/m$^2$) for ten minutes. Then, a quantitative analysis of gas contained in the tank was conducted by gas chromatogram mass spectrometry (GCMS). The result of the analysis shows detected gases are O$_2$, H$_2$, and CO. The CO gas is produced by CO$_2$ reduction. CO$_2$ photoreduction efficiencies are calculated from CO quantities measured for the sample cells in example 1 and shown in relative values scaled to the CO quantity produced for the cell of the comparative example, which is assumed to be 1.00.

As shown in FIG. 12, the smaller the area ratio of the through-holes 52 are, the higher CO$_2$ photoreduction efficiencies can be attained compared to the comparative example, if the equivalent circle diameters of the through-holes 52 are the same in example 1. More specifically, regardless of the equivalent circle diameter of the through-hole 52, a high CO$_2$ photoreduction efficiency can be attained if the area ratio of the through-hole 52 is 10, 20, or 30%. This is a result of minimizing the area ratio of the through-hole 52. That is, this is a result of achieving an efficiency increase by H$^+$ transfer improvement and avoiding an efficiency decrease caused by light absorption loss by controlling the area decrease of the multi-junction photovoltaic cell 17. For the cases with the area ratio of 40% or more, however, the achieved photoreduction efficiencies are less than that of the comparative example because the efficiency decrease caused by light absorption loss outweighs the efficiency increase by H$^+$ transfer improvement. From the result of example 1, it can be said that the area ratio of the through-hole 52 needs to be 40% or less, more preferably 10% or less. However, this area ratio do not apply to cases in which light diffraction effect or scattering effect is available, as described for a second embodiment later.

In example 1, the larger the equivalent circle diameter of the through-holes 52, the higher the CO$_2$ photoreduction efficiency attained, compared to the comparative example, if the area ratios of the through-holes 52 are the same. This is because a structure including a through-hole 52 with a large equivalent circle diameter can have a large processing range (processing area) per unit area, and the effect of damage caused by the processing can be reduced.

As described above, in the first embodiment, higher CO$_2$ photoreduction efficiencies compared with the comparative example can be attained by adjusting both the equivalent circle diameter and area ratio of the through-hole 52 for the cases in which the through-hole 52 is formed as an ion transfer pathway.

2-2. Second Embodiment

Referring to FIGS. 13 to 19, a photochemical reaction device of a second embodiment will be described below.

According to the experimental result shown in FIG. 12, CO$_2$ photoreduction efficiency for a case in which the through-hole 52 is formed as an ion transfer pathway is determined mainly by not only the H$^+$ transfer efficiency but also the light absorption amount by the multi-junction photovoltaic cell 17. This is because, if the through-hole 52 is formed in the photoelectrochemicalcell, the area of the multi-junction photovoltaic cell 17 decreases, which leads to a reduction in the light absorption amount. As a result, the number of electrons and holes created by light decreases and the decrease leads to a reduction in reaction efficiency of the oxidation-reduction reaction. Suppression of light absorption loss at the multi-junction photovoltaic cell 17 caused by forming the through-hole 52 is thus needed.

The second embodiment is an example in which the light absorption loss associated with the decrease in the area of the multi-junction photovoltaic cell 17 is suppressed by adjusting the size, shape, or structure of the through-hole 52. The second embodiment will be described in detail below. In the description of the second embodiment, description of the same or similar features as the first embodiment will be omitted and only differences will be described.

Structure of Second Embodiment

A structure of a photochemical reaction device of the second embodiment will be described first below.

Figure 13:
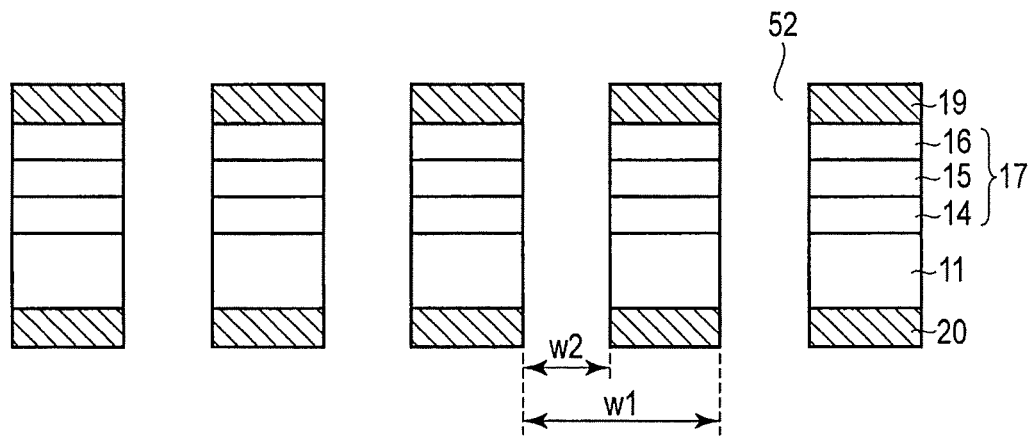
FIG. 13 is a cross-sectional view showing a structure of a photochemical reaction device of a second embodiment.

FIG. 13 is a cross-sectional view, taken along the line A-A in FIG. 9, showing a structure of a photochemical reaction device of the second embodiment.

As shown in FIG. 13, one of the differences between first embodiment and the second embodiment is that sizes of the through-holes 52 are precisely defined. More specifically, a pitch w1 of the through-hole 52 is 3 μm or less, or an equivalent circle diameter w2 of the through-hole 52 is 1 μm or less. That is, the through-hole 52 in the second embodiment is formed comparatively finely. Reasons for this will be described below.

Figure 14:
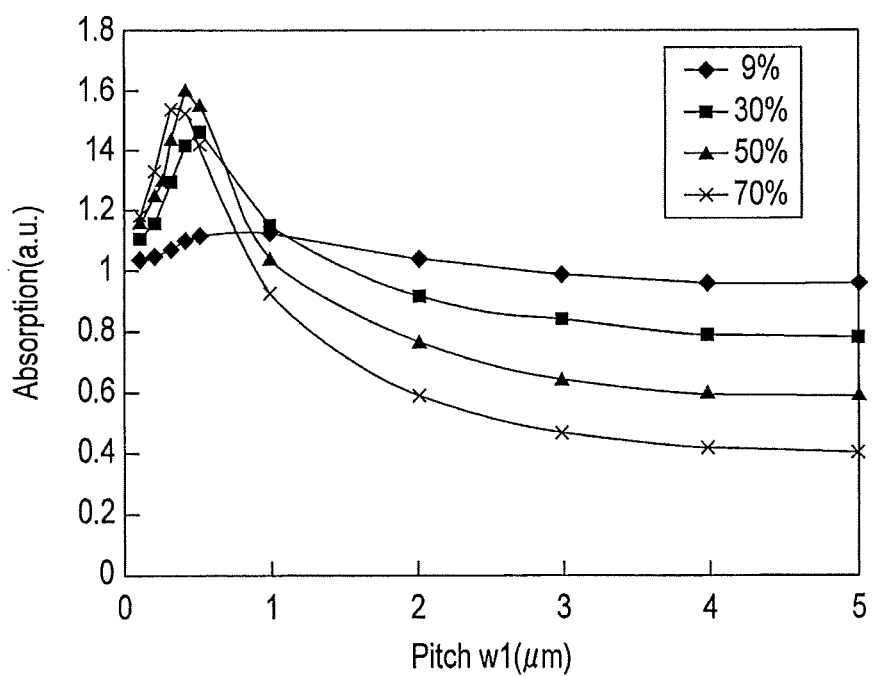
FIG. 14 is a graph showing a relation between pitch of through-holes and a light absorption rate by a multi-junction photovoltaic cell in the photochemical reaction device of the second embodiment.
Figure 15:
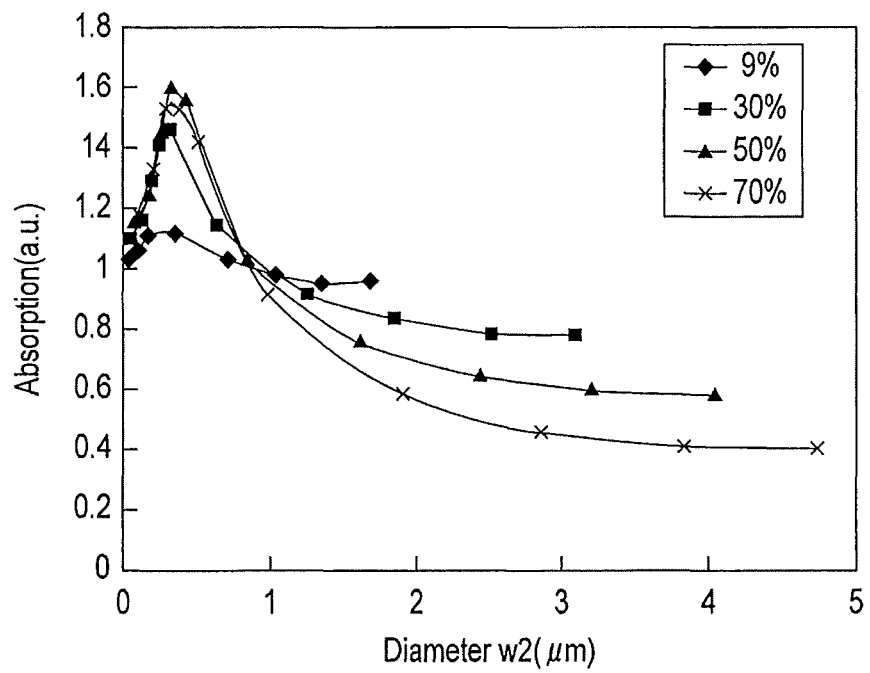
FIG. 15 is a graph showing a relation between equivalent circle diameters of the through-holes and a light absorption rate by the multi-junction photovoltaic cell in the photochemical reaction device of the second embodiment.

FIG. 14 is a graph showing a relation between the pitch w1 of the through-holes 52 and a light absorption rate by a multi-junction photovoltaic cell 17 in the photochemical reaction device of the second embodiment. FIG. 15 is a graph showing a relation between the equivalent circle diameter w2 of the through-holes 52 and the light absorption rate by the multi-junction photovoltaic cell 17 in the photochemical reaction device of the second embodiment.

In FIGS. 14 and 15, the sunlight absorption amount measured by RCWA (Rigorous Coupled Wave Analysis) is shown for a case in which a plurality of the through-holes 52 are arranged in a square lattice in an a-Si layer with a thickness of 550 nm. More specifically, a light absorption rate $\alpha(\lambda)$ for incident light perpendicularly entering the surface of the sample and with a wavelength of 300 nm to 1000 nm is calculated using Diffract MD (manufactured by Rsoft) and the sunlight absorption amount $A=\Sigma\alpha(\lambda)\times I(\lambda)$ is calculated by multiplying sunlight spectrum $I(\lambda)$ to the light absorption rate. FIGS. 14 and 15 show the sunlight absorption amounts in relative values scaled to a sunlight absorption amount of a photochemical reaction device including no through-hole 52 (hereinafter, a comparative example), which is assumed to be 1. The computing is done for the cases in which the area ratios of the through-hole 52 are 9, 30, 50, and 70%.

As shown in FIG. 14, the light absorption rate decreases (to 1 or less) compared with the comparative example as the pitch w1 of the through-hole 52 increases. Similarly, as shown in FIG. 15, the light absorption rate decreases compared with the comparative example as the equivalent circle diameter w2 of the through-hole 52 increases. This is because the light absorption amount decreases by the volume of the through-hole 52 due to a geometrical interaction between incident light and through-hole structure.

However, if the pitch w1 is 3 μm or less or the equivalent circle diameter w2 is 1 μm, there is no decrease in the absorption amount compared with the comparative example and a high absorption amount can be achieved. This is because incident light is diffracted and scattered in the a-Si layer by the formed through-hole structure. That is, this is because, by diffraction and scattering, the incident light enters the a-Si layer, its optical path length is lengthened, and the light absorption amount by the a-Si layer increases.

Though a plurality of the through-holes 52 arranged in a square lattice is described above, using a triangular arrangement leads to a similar result. The planar shape of the through-hole 52 is not limited to a circular shape. It may be elliptical, triangular, or square. The planar shape of the through-hole 52 need neither be a regular shape nor in a regular arrangement. If it has a structure with a cycle and fluctuation in diameters, a diffraction effect is attainable. Even if it has a random structure, the light absorption amount can be increased due to a light scattering effect.

Manufacturing Method of Second Embodiment

Next, a manufacturing method of the photochemical reaction device of the second embodiment will be described below.

As with the first embodiment, a photoelectrochemicalcell made of a laminated body of the substrate 11, the reflecting layer 12, the reduction electrode layer 13, the multi-junction photovoltaic cell 17, the oxidation electrode layer 18, the oxidation catalyst layer 19, and the reduction catalyst layer 20 is formed.

Next, a through-hole 52 which penetrates the photoelectrochemicalcell from the oxidation catalyst layer 19 to the reduction catalyst layer 20 is formed.

More specifically, a resist is coated on the oxidation catalyst layer 19 and baked first. Next, light or an electron beam is irradiated on the resist with exposure equipment or electron beam lithography and a resist pattern is formed by pre-bake and development processing.

Next, layers from the oxidation catalyst layer 19 to the reduction catalyst layer 20 are etched by RIE (Reactive Ion Etching) using the resist pattern as a mask. That is, the oxidation catalyst layer 19, the oxidation electrode layer 18, the multi-junction photovoltaic cell 17, the reduction electrode layer 13, the reflecting layer 12, the substrate 11, and the reduction catalyst layer 20 are etched in this order. Then, the resist is removed by an ashing processing.

The through-hole 52 is thus formed in the substrate 11, the reflecting layer 12, the reduction electrode layer 13, the multi-junction photovoltaic cell 17, the oxidation electrode layer 18, the oxidation catalyst layer 19, and the reduction catalyst layer 20. Next, disposing the photoelectrochemical-cell to which the through-hole 52 is formed in the electrolytic tank 31 completes an assembly of the photochemical reaction device.

Figure 16:
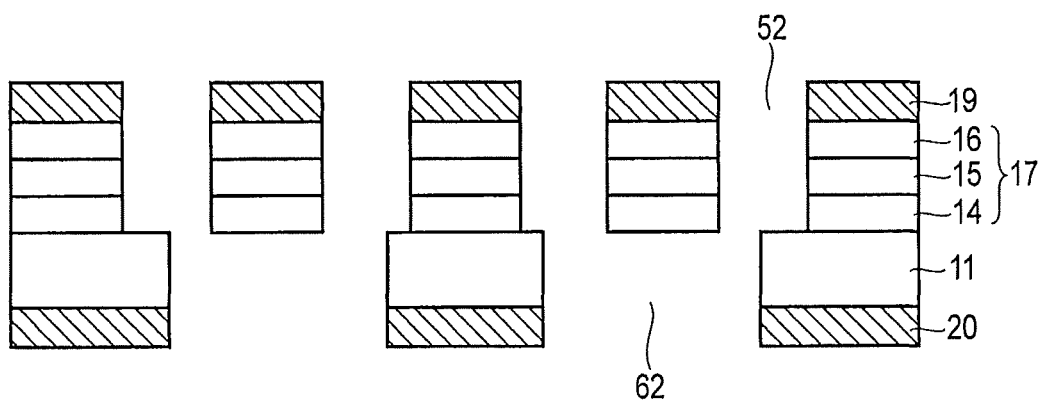
FIG. 16 is a cross-sectional view showing another structure of the photochemical reaction device of the second embodiment.

The substrate 11 may be made of a material that is hard to be processed by dry etching such as RIE due to its large thickness. Forming a fine through-hole 52 according to the second embodiment to the substrate 11 therefore becomes difficult. As shown in FIG. 16, from the viewpoint of manufacturing, the through-hole 52 may be formed with a method described below.

A resist is coated on the oxidation catalyst layer 19 (on the front surface) and baked first. Next, light or an electron beam is irradiated on the resist with exposure equipment or electron beam lithography and a resist pattern is formed by pre-bake and development processing.

Next, layers from the oxidation catalyst layer 19 to the reflecting layer 12 are etched by RIE using the resist pattern as a mask. That is, the through-hole 52 is formed by etching the oxidation catalyst layer 19, the oxidation electrode layer 18, the multi-junction photovoltaic cell 17, the reduction electrode layer 13, and the reflecting layer 12 from the front surface side in this order. The substrate 11 and the reduction catalyst layer 20 are not etched at this moment. Then, the resist is removed by an ashing processing.

Next, a resist is formed on and protects exposed surfaces of the formed oxidation catalyst layer 19, oxidation electrode layer 18, multi-junction photovoltaic cell 17, reduction electrode layer 13, and reflecting layer 12. Then, a resist is coated on the reduction catalyst layer 20 (on the back surface) and baked. Next, light or an electron beam is irradiated on the resist with exposure equipment or electron beam lithography and a resist pattern is formed by pre-bake and development processing.

Next, layers from the reduction catalyst layer 20 to the substrate 11 are etched by wet etching using the resist pattern as a mask. That is, the reduction catalyst layer 20 and the substrate 11 are etched from the back surface side in this order.

In this process, the substrate 11 and the reduction catalyst layer 20 are etched isotropically by wet etching. As shown in FIG. 16, a through-hole 62 that has a larger equivalent circle diameter than the through-hole 52 is thus formed in the substrate 11 and the reduction catalyst layer 20.

Next, the resist over the oxidation catalyst layer 19, oxidation electrode layer 18, multi-junction photovoltaic cell 17, reduction electrode layer 13, and reflecting layer 12 and the resist over the reduction catalyst layer 20 are removed by applying ultrasonic cleaning in an organic solvent.

The through-hole 52 is thus formed in the oxidation catalyst layer 19, the oxidation electrode layer 18, the multi-junction photovoltaic cell 17, the reduction electrode layer 13, and the reflecting layer 12 and the through-hole 62 is formed in the reduction catalyst layer 20 and the substrate 11. Next, disposing the photoelectrochemicalcell to which the through-hole 52 is formed in the electrolytic tank 31 completes an assembly of the photochemical reaction device.

Effect of Second Embodiment

By the above-described second embodiment, effects similar to the effects by the first embodiment can be attained.

According to the second embodiment, a pitch w1 of the through-holes 52 formed in the photoelectrochemicalcell is set to 3 µm or less and an equivalent circle diameter w2 is set to 1 µm or less. With this arrangement, incident light can be diffracted and scattered. As a result, because the incident light entering on a surface of the through-hole 52 also enters the multi-junction photovoltaic cell 17, the light absorption loss by the multi-junction photovoltaic cell 17 can be lessened. Moreover, it is possible to increase the light absorption amount by the multi-junction photovoltaic cell 17 due to a lengthened optical path length.

The $CO_2$ photoreduction efficiency in the second embodiment will be described below.

FIG. 17 is a table of an experimental result showing $CO_2$ photoreduction efficiency in the example 2 in comparison with the comparative example. More specifically, the table shows $CO_2$ photoreduction efficiencies for example 2 (2-1 to 2-4) as relative values scaled to the $CO_2$ photoreduction efficiency of the comparative example, which is assumed to be 1.00. Details of FIG. 17 will be described below.

Example 2 is an example of the photoelectrochemicalcell in the photochemical reaction device of the second embodiment. More specifically, the photoelectrochemicalcell of example 2 has the through-hole 52 through which only $H^+$ can be moved and the equivalent circle diameter of which is relatively small. In example 2, four photoelectrochemicalcells (sample cell numbers 2-1 to 2-4), the through-holes 52 of which have equivalent circle diameters of 0.1, 0.5, 1.0, and 2.0 µm respectively and area ratios of 30%, were produced and their $CO_2$ photoreduction efficiencies were evaluated. These photoelectrochemicalcells in example 2 were produced as described below.

First, a structure that has the multi-junction photovoltaic cell 17 including a pin-type a-Si layer, a-SiGe layer, and a-SiGe layer, the oxidation electrode layer 18 made from ITO and formed on the front surface of the multi-junction photovoltaic cell 17, the reduction electrode layer 13 made from ZnO and formed on the front surface of the multi-junction photovoltaic cell 17, the reflecting layer 12 made from Ag and formed on the back surface of the reduction electrode layer 13, and the SUS substrate 11 formed on the back surface of the reflecting layer 12 is prepared. In this configuration, the thickness of the multi-junction photovoltaic cell 17 is 500 nm, the thickness of the oxidation electrode layer 18 is 100 nm, the thickness of the reduction electrode layer 13 is 300 nm, the thickness of the reflecting layer 12 is 200 nm, and the thickness of the SUS substrate 11 is 1.5 mm.

Next, the oxidation catalyst layer 19 made from Nickel oxide is formed on the front surface of the oxidation electrode layer 18 by a sputtering method. On the back surface of the SUS substrate 11, the reduction catalyst layer 20 made from Ag is formed with a vacuum evaporation method. In this process, the thickness of the oxidation catalyst layer 19 is 50 nm and the thickness of the reduction catalyst layer 20 is 100 nm.

A laminated body (cell) of the substrate 11, the reflecting layer 12, the reduction electrode layer 13, the multi-junction photovoltaic cell 17, the oxidation electrode layer 18, the oxidation catalyst layer 19, and the reduction catalyst layer 20 is thus formed.

Next, the through-hole 52 and the through-hole 62 are formed in the cell. The through-hole 52 and through-hole 62 are formed as follows.

First, a positive resist for i-ray lithography or a positive electron beam resist is coated on the oxidation catalyst layer 19 (on the front surface) by spin coat and then baked. Next, light or an electron beam is irradiated on the resist with exposure equipment or electron beam lithography and a resist pattern of an opening pattern in a triangular lattice is formed by pre-bake and development processing.

Next, layers from the oxidation catalyst layer 19 to the reflecting layer 12 are etched by inductively-coupled plasma (ICP) RIE with use of a chlorine-argon mixed gas using the resist pattern as a mask. That is, the through-hole 52 is formed by etching the oxidation catalyst layer 19, the oxidation electrode layer 18, the multi-junction photovoltaic cell 17, the reduction electrode layer 13, and the reflecting layer 12 from the front surface side in this order. The substrate 11 and the reduction catalyst layer 20 are not etched at this moment. Then, the resist is removed by an ashing processing.

Next, a resist is formed on and protects exposed surfaces of the formed oxidation catalyst layer 19, oxidation electrode layer 18, multi-junction photovoltaic cell 17, reduction electrode layer 13, and reflecting layer 12. Then, a positive resist for i-line lithography is coated on the reduction catalyst layer 20 (on the back surface) and baked. Next, light or an electron beam is irradiated on the resist with exposure equipment or electron beam lithography and a resist pattern is formed by pre-bake and development processing.

Next, layers from the reduction catalyst layer 20 to the substrate 11 are etched by wet etching by use of an acid using the resist pattern as a mask. That is, the reduction catalyst layer 20 and the substrate 11 are etched from the back surface side in this order.

The substrate 11 and the reduction catalyst layer 20 are etched isotropically by wet etching. A through-hole 62 that has a larger equivalent circle diameter than the through-hole 52 is therefore formed in the substrate 11 and the reduction catalyst layer 20. The through-hole 62 has an equivalent circle diameter of 15 µm and an area ratio of 10%. A plurality of the through-holes 62 are arranged in a triangular lattice.

Next, the resist over the oxidation catalyst layer 19, oxidation electrode layer 18, multi-junction photovoltaic cell 17, reduction electrode layer 13, and reflecting layer 12 and the resist over the reduction catalyst layer 20 are removed by applying ultrasonic cleaning in an organic solvent.

Next, the cell to which the through-hole 52 is formed is cut into a square shape and the edges of the cell are sealed with epoxy resin so that the area of exposed part is 1 $cm^2$. Then, an image of the cell is taken with an optical microscope or scanning electron microscope from an angle of view such that about one hundred through-holes 52 are captured and the equivalent circle diameter and area ratio of the through-hole 52 of each cell are measured with image processing software. By the above process, the photoelectrochemicalcells (sample cell numbers 2-1 to 2-4) of example 2 were produced.

In contrast, the photoelectrochemicalcell of the comparative example is a photoelectrochemicalcell that has no through-hole 52 (and no through-hole 62) and has the same structure as the cell of example 2 except the through-hole 52.

The CO2 photoreduction efficiency was measured by a method to be described below. First, the cell was dipped in a closed-system tank (electrolytic tank 31) which contained a solution of 0.1 M (mol/l) $KHCO_3$ produced by bubbling $CO_2$ gas for ten minutes. Next, light was irradiated on the cell from the side where the oxidation catalyst layer 19 exists by a solar simulator (AM1.5, 1000 $W/m^2$) for ten minutes. Then, a quantitative analysis of gas contained in the tank was conducted by gas chromatogram mass spectrometry (GCMS). The result of the analysis shows that detected gases are $O_2$, $H_2$, and CO. The CO gas is produced by $CO_2$ reduction. $CO_2$ photoreduction efficiencies are calculated from CO quantities measured for the sample cells in example 2 and shown in relative values scaled to the CO quantity produced for the cell of the comparative example, which is assumed as 1.00.

As shown in FIG. 17, in example 2, if the equivalent circle diameter is 0.1, 0.5, or 1.0 μm, a high $CO_2$ photoreduction efficiency can be achieved compared with the comparative example. This is because not only an efficiency increase by $H^+$ transfer improvement is achieved but also the light absorption amount by the multi-junction photovoltaic cell 17 is increased through the diffraction and scattering of incident light caused by a relatively shortened equivalent circle diameter. In particular, a higher $CO_2$ photoreduction efficiency can be attained for the case of sample cell number 2-2 (with the equivalent circle diameter of 0.5 μm). However, if the equivalent circle diameter is 2.0 μm, the diffraction effect diminishes and an attainable advantage is smaller than the comparative example.

As described above, in example 2 of the second embodiment, a high $CO_2$ photoreduction efficiency compared with the comparative example can be attained by adjusting the equivalent circle diameter of the through-hole 52 to 1 μm or less.

FIG. 18 is a table of an experimental result showing $CO_2$ photoreduction efficiency of example 3 in comparison with the comparative example. More specifically, the table shows $CO_2$ photoreduction efficiencies for example 3 (3-1 to 3-2) as relative values scaled to the $CO_2$ photoreduction efficiency of a comparative example, which is assumed to be 1.00. FIG. 19 is a plan view showing a structure of the photochemical reaction device of example 3. FIG. 20 is a cross-sectional view showing the structure of the photochemical reaction device of example 3. Details of FIGS. 18 to 20 will be described below.

Example 3 is an example of the photoelectrochemicalcell in the photochemical reaction device of the second embodiment. More specifically, the photoelectrochemicalcell of example 2 has the through-hole 52 through which only $H^+$ can be moved and the equivalent circle diameter of which is relatively small.

As shown in FIGS. 19 and 20, in the photochemical reaction device of example 3, the equivalent circle diameter and the arrangement of a plurality of the through-holes 52 are random. In example 3, furthermore, the electrolytic solution touching the reduction catalyst layer 20 is different from the electrolytic solution touching the oxidation catalyst layer 19 and a photochemical reaction is created by irradiating light from the side where the reduction catalyst layer 20 exists.

In example 3, two photoelectrochemicalcells, a photoelectrochemicalcell having an ion exchange membrane 43 inside the through-hole 52 (sample cell number 3-1) and a photoelectrochemicalcell having no ion exchange membrane (sample cell number 3-2), were produced and their $CO_2$ photoreduction efficiencies were evaluated. Gas products detected in the above evaluation were also analyzed. These photoelectrochemicalcells in the example 3 were produced as described below.

First, a structure that has the multi-junction photovoltaic cell 17 including an InGaP layer (a third photovoltaic cell 16), an InGaAs layer (a second photovoltaic cell 15), and a Ge layer (a first photovoltaic cell 14), all having p-n junctions, the reduction electrode layer 17 made from ITO and formed on the front surface (light incidence surface) of the multi-junction photovoltaic cell 17, the oxidation electrode layer 18 made from Au and formed on the back surface of the multi-junction photovoltaic cell 17 is prepared. In this configuration, p-type layers of the multi-junction photovoltaic cell 17 are disposed on the side facing the oxidation electrode layer 18 and n-type layers of the multi-junction photovoltaic cell 17 are disposed on the side facing the reduction electrode layer 13.

More specifically, the multi-junction photovoltaic cell 17 includes n-InGaAs (contact layer), n-AlInP (window layer), p-InGaP, p-AlInP (Back Surface Field (BSF) layer), p-AlGaAs (tunneling layer), p-InGaP (tunneling layer), n-InGaP (window layer), n-InGaAs, p-InGaP (BSF layer), p-GaAs (tunneling layer), n-GaAs (tunneling layer), n-InGaAs, and p-Ge (Substrate).

Next, the oxidation catalyst layer 19 made from Nickel oxide is formed on the back surface of the oxidation electrode layer 18 by a sputtering method. On the front surface of the reduction electrode layer 13, the reduction catalyst layer 20 made from Ag is formed with a vacuum evaporation method. In this process, the thickness of the oxidation catalyst layer 19 is 50 nm and the thickness of the reduction catalyst layer 20 is 15 nm.

The open circuit voltage of the cell when light is irradiated from the side facing the reduction catalyst layer 20 was measured by a solar simulator (AM1.5, 1000 $W/m^2$) and the measured value was 2.4 V.

A laminated body (cell) of the reduction electrode layer 13, the multi-junction photovoltaic cell 17, the oxidation electrode layer 18, the oxidation catalyst layer 19, and the reduction catalyst layer 20 is thus formed.

Next, the through-hole 52 and the through-hole 62 are formed in the cell. The through-hole 52 and through-hole 62 are formed as follows.

First, a positive resist for i-line lithography is coated on the reduction catalyst layer 20 (on the front surface) by spin coat and baked on a hot plate. Next, a quartz stamper, which is a mold, is prepared. A pattern of the stamper is produced by copying a pattern formed by the self-organization of a block copolymer. The pattern formed on the stamper has randomly-arranged pillars which have a wide range of diameters with an average equivalent circle diameter of 120 nm (with a standard deviation of 31 nm). In this process, the surface of the stamper is coated with a fluorine mold-releasing agent such as perfluoropolyether as a pre-process for mold-releasing to lower the surface energy and improve the releasability of the stamper.

Next, the stamper is pressed against the resist at the temperature of 128° C. and the pressure of 60 kN using a heater plate press. After the temperature settles to room temperature, releasing the stamper vertically forms a reverse pattern of the mold on the resist. By this process, a resist pattern which has openings is created. Using this resist pattern as an etching mask, the reduction catalyst layer 20 made from Ag is etched by ion milling and the reduction electrode layer 13 made from ITO is etched by wet etching by use of an oxalic acid. The InGaP layer 16 and InGaAs layer 15 of the multi-junction photovoltaic cell 17 is etched by ICP-RIE by use of chlorine gas. The through-hole 52 is thus formed in the reduction catalyst layer 20, the reduction electrode layer 13, the InGaP layer 16, and the InGaAs layer 15. The Ge layer 14, the oxidation electrode layer 18, and the oxidation catalyst layer 19 are not etched at this moment. Then, the resist is removed by an ashing processing.

Next, a resist is formed on and protects exposed surfaces of the formed reduction catalyst layer 20, reduction electrode layer 13, InGaP layer 16, and InGaAs layer 15. Then, a positive resist for i-ray lithography is coated on the oxidation catalyst layer 19 (on the back surface) and baked. Next, an exposure process and development process are executed to the resist and a resist pattern of opening shapes is formed.

Next, the oxidation catalyst layer 19 made from Nickel oxide and the oxidation electrode layer 18 made from Au are etched by ion milling and the Ge layer 14 is etched by wet etching by use of an acid. The through-hole 62 is thus formed in the oxidation catalyst layer 19, the oxidation electrode layer 18, and the Ge layer 14. As a result, the through-hole 62 has an equivalent circle diameter of 30 µm and an area ratio of 15%. The plurality of the through-holes 62 are arranged in a triangular lattice.

Next, the resist over the reduction catalyst layer 20, reduction electrode layer 19, InGaP layer 16, and InGaAs layer 15 and the resist over the oxidation catalyst layer 19 are removed by applying ultrasonic cleaning in an organic solvent.

In the case of the sample cell number 3-1, a portion of the through-holes 52 and 62 are filled with an ion exchange membrane 43. More specifically, the ion exchange membrane 43 is formed inside the through-holes 52 and 62 by dipping in the Nafion solution and drying the cell.

Next, the cell to which the through-hole 52 is formed is cut into a square shape and the edges of the cell are sealed with epoxy resin so that the area of exposed part is 1 cm$^2$. By the above process, the photoelectrochemicalcells (sample cell numbers 3-1) was produced.

The photoelectrochemicalcell of the sample cell number 3-2 is a photoelectrochemicalcell that has no ion exchange membrane 43 inside the through-hole 52 (and the through-hole 62) and has a similar structure to the photoelectrochemicalcell of the sample cell number 3-1 except the ion exchange membrane.

In contrast, the photoelectrochemicalcell of the comparative example is a photoelectrochemicalcell that has no through-hole 52 (and the through-hole 62) or ion exchange membrane 43 and has the same structure as the cell of example 3 (sample cell numbers 3-1 and 3-2) except the through-hole 52.

Figure 21:
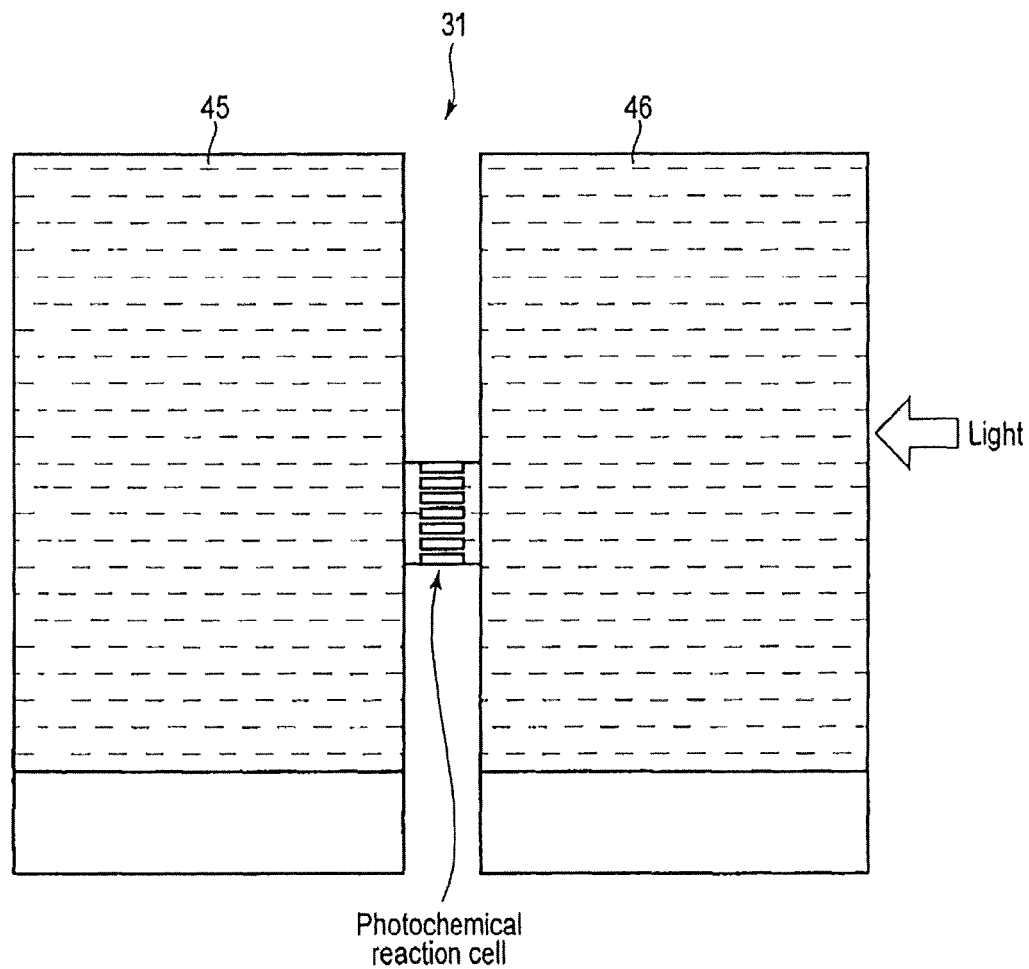
FIG. 21 is a cross-sectional view showing an electrolytic tank to measure the photochemical reaction device in example 3 and the comparative example.

FIG. 21 is a cross-sectional view showing an electrolytic tank 31 to measure the photochemical reaction device of example 3 and the comparative example.

As shown in FIG. 21, the photoelectrochemicalcells of example 3 and the comparative example are set to the central part of the electrolytic tank 31, which is an H-shaped closed-system cell. In other words, the electrolytic tank 31 has an oxidation reaction electrolytic tank 45, a reduction reaction electrolytic tank 46, and a bridge part with a narrow width. The photoelectrochemicalcell is disposed to the narrow bridge part. The photoelectrochemicalcell is set so that the oxidation catalyst layer 19 of the cell faces the oxidation reaction electrolytic tank 45 and the reduction catalyst layer 20 of the cell faces the reduction reaction electrolytic tank 46. For an electrolytic solution in the oxidation reaction electrolytic tank 45, a sodium sulfate aqueous solution of 0.5 mol/L is used. For an electrolytic solution in the reduction reaction electrolytic tank 46, a 2-aminoethanol (monoethanolamine) aqueous solution (40 wt %), produced by bubbling $CO_2$ gas for two hours at a temperature of 40° C., is used.

The CO2 photoreduction efficiency and gaseous materials were measured by a method to be described below. First, light was irradiated on the cell from the side where the reduction catalyst layer 20 exists by a solar simulator (AM1.5, 1000 W/m$^2$) for ten minutes. Then, a quantitative analysis of gas contained in each tank was conducted by the gas chromatogram mass spectrometry (GCMS). $CO_2$ photoreduction efficiencies are calculated from CO quantities measured for the sample cells in example 3 and shown as relative values scaled to the CO quantity produced for the cell of the comparative example, which is assumed to be 1.00.

As shown in FIG. 18, in the cell of the sample cell number 3-1, dissimilar to the cell of the sample cell number 3-2, only H$^+$ can move due to an effect of the ion exchange membrane 43 disposed in the through-hole 52 (and the through-hole 62). Due to this structure, materials produced in each tank were detected separately. More specifically, $H_2$ and $CO_2$ were detected in the reduction reaction electrolytic tank 46 and $O_2$ was detected in the oxidation reaction electrolytic tank 45.

Even in the case that a plurality of the through-holes 52 (and the through-holes 62) have random sizes (equivalent circle diameters) and a random arrangement as in example 3, a $CO_2$ photoreduction efficiency that is sufficiently high compared with the comparative example can be attained. Moreover, in example 3, a $CO_2$ photoreduction efficiency that is high compared with example 2 can also be attained. This is because, if the electrolytic solution in the oxidation reaction electrolytic tank 45 is separated from the electrolytic solution in the reduction reaction electrolytic tank 46 with a cell, the $CO_2$ photoreduction reaction extremely decreases in the comparative example where there is no transfer pathway (the through-hole 52 and through-hole 62) for H. This means that, as the cell size increases, H$^+$ movement is impeded and the attainable photoreaction efficiency decreases for a photoelectrochemicalcell having no transfer pathway for H$^+$. As described above, a high photoreaction efficiency can be attained for a large-size cell by providing an H$^+$ transfer pathway.

Variations of Second Embodiment

Next, a variation of the photochemical reaction device of the second embodiment will be described below.

Figure 22:
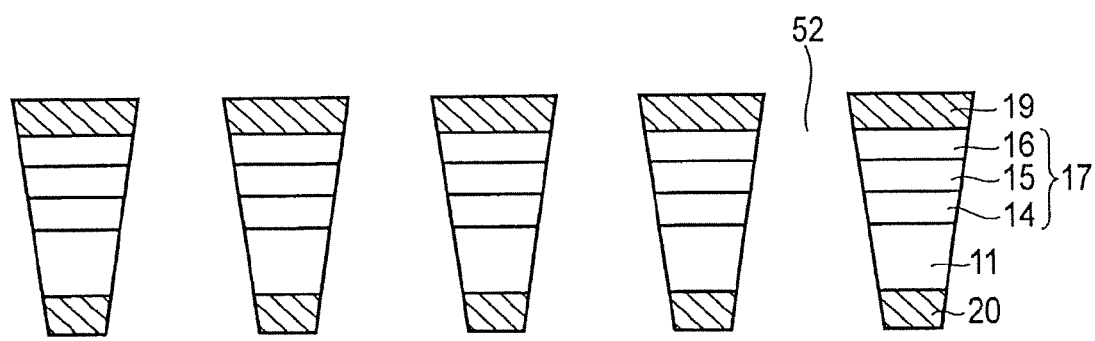
FIG. 22 is a cross-sectional view showing a structure of variation 1 of the photochemical reaction device of the second embodiment.
Figure 23:
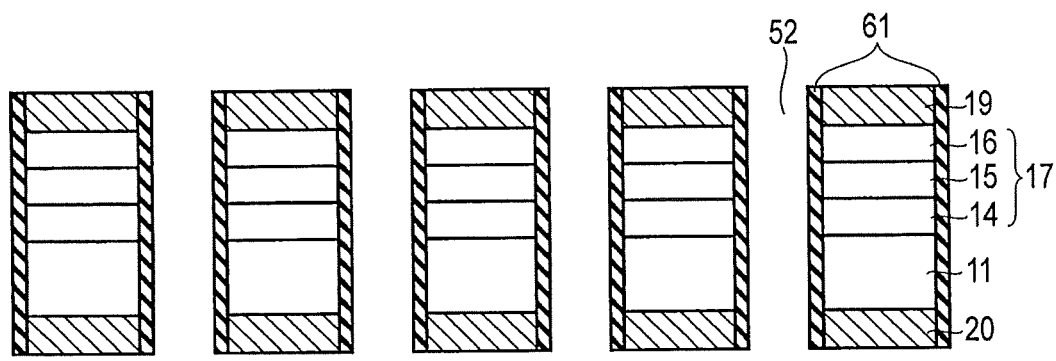
FIG. 23 is a cross-sectional view showing a structure of a variation 2 of the photochemical reaction device of the second embodiment.

FIGS. 22 and 23 are cross-sectional views showing structures of variation 1 and variation 2 of the photochemical reaction device of the second embodiment. Only differences from the above-described structure of the photochemical reaction device of the second embodiment will be described.

As shown in FIG. 22, in the variation 1 of the photochemical reaction device of the second embodiment, the through-hole 52 is formed so that its equivalent circle diameter w2 becomes larger from the front surface side (incidence surface side) toward the back surface side. That is, the through-hole 52 is formed in a tapered shape such that its equivalent circle diameter w2 becomes larger from the oxidation catalyst layer 19 toward the reduction catalyst layer 20. Due to this structure, the equivalent circle diameter of the through-hole 52 in the multi-junction photovoltaic cell 17 at the front surface is larger than the equivalent circle diameter of the through-hole 52 at the back surface. It is preferable that the equivalent circle diameter of the through-hole 52 at the back surface of the multi-junction photovoltaic cell 17 is 10 to 90% of the equivalent circle diameter of the through-hole 52 at the front surface.

The through-hole 52 with a tapered shape can be formed by adjusting the etching gas in the etching process by ICP-RIE. More specifically, the through-hole 52 with a tapered shape is formed by isotropic etching using a chlorine-argon mixed gas with a high mixture ratio of argon gas as an etching gas.

By forming the through-hole 52 in a tapered shape, a GI (Graded Index) effect, i.e., applying a gradient to the distribution of refractive index from the front surface side to the back surface side, can be provided. With such GI effect, an antireflection effect, by which a light reflection component created upon light incidence is suppressed, can be attained. That is, because more light enters the multi-junction photovoltaic cell 17, it is possible to absorb more light. An improvement of 10 to 15% over the photoreduction efficiency achieved by the cells in example 2 due to the antireflection effect is indicated in the result of a photoreduction efficiency measurement, which is conducted under the same conditions as in example 2.

As shown in FIG. 23, a protective layer 61 is formed on the interior surface of the through-hole 52 in the variation 2 of the photochemical reaction device of the second embodiment. In other words, the protective layer 61 is formed on sidewalls of the substrate 11, multi-junction photovoltaic cell 17, oxidation catalyst layer 19, and reduction catalyst layer 20 inside the through-hole 52. The protective layer 61 is made of a dielectric (insulator) thin film such as $SiO_2$, $TiO_2$, $ZrO_2$, $Al_2O_3$, and $HfO_2$. The thickness of the protective layer 61 is, for example, around 30 nm.

The protective layer 61 is formed on the interior surface of the through-hole 52 and on the resist by ALD (Atomic Layer Deposition) or CVD (Chemical Vapor Deposition) after the etching process by ICP-RIE and before the removal of the resist over the oxidation catalyst layer 19. Thus, by removing the protective layer 61 over the resist and the resist, the protective layer 61 is formed only on the interior surface of the through-hole 52.

A method for forming the protective layer 61 is not limited to the ALD or CVD method. The dipping method, which includes dipping of a cell into a solution including metallic ions and heat treatment, is also effective.

By forming the protective layer 61 as a sidewall of the through-hole 52, it becomes possible to suppress the leakage of electrons and holes from the multi-junction photovoltaic cell 17 and prevent the multi-junction photovoltaic cell 17 from being corroded by a solution. An improvement of 5 to 10% over the photoreduction efficiency achieved by the cells of example 2 due to the leakage prevention is indicated in the result of a photoreduction efficiency measurement, which is conducted under the same conditions as in example 2.

2-3. Third Embodiment

Referring to FIGS. 24 to 27, a photochemical reaction device of a third embodiment will be described below. A photochemical reaction device of the third embodiment is an example in which a photoelectrochemicalcell is applied to a tubular (pipe-like) piping. With this structure, it becomes possible to resolve $CO_2$, to easily transfer chemical compounds produced in the oxidation catalyst layer 19 and the reduction catalyst layer 20, and to use the compounds as chemical energy. The third embodiment will be described in detail below. In the description of the third embodiment, description of the same or similar features as the photochemical reaction device of the first embodiment will be omitted and only differences will be described.

Structure of Third Embodiment

A structure of a photochemical reaction device of the third embodiment will be described first below.

Figure 24:
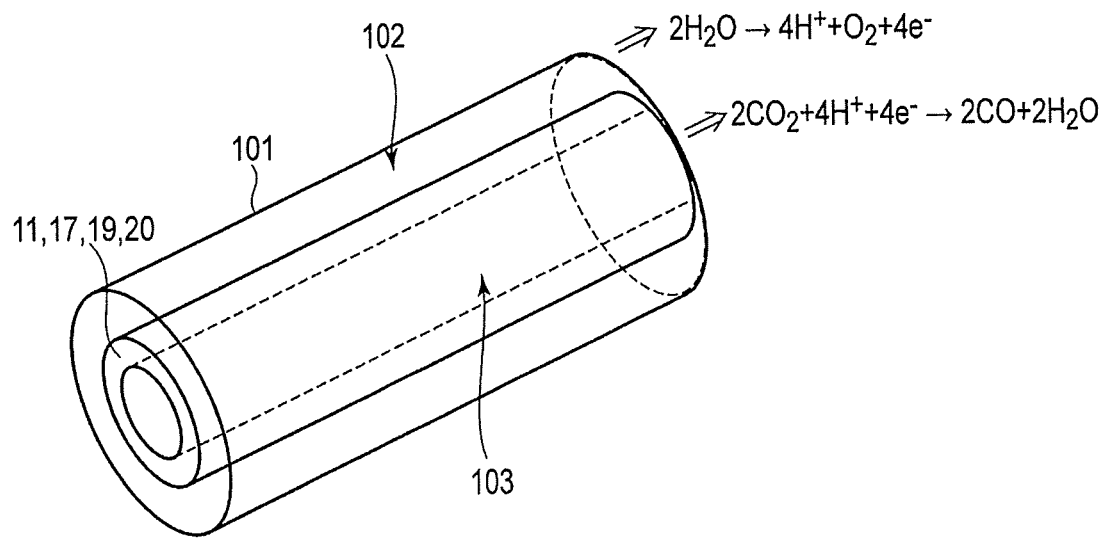
FIG. 24 is a perspective view showing a structure of the photochemical reaction device of the third embodiment.
Figure 25:
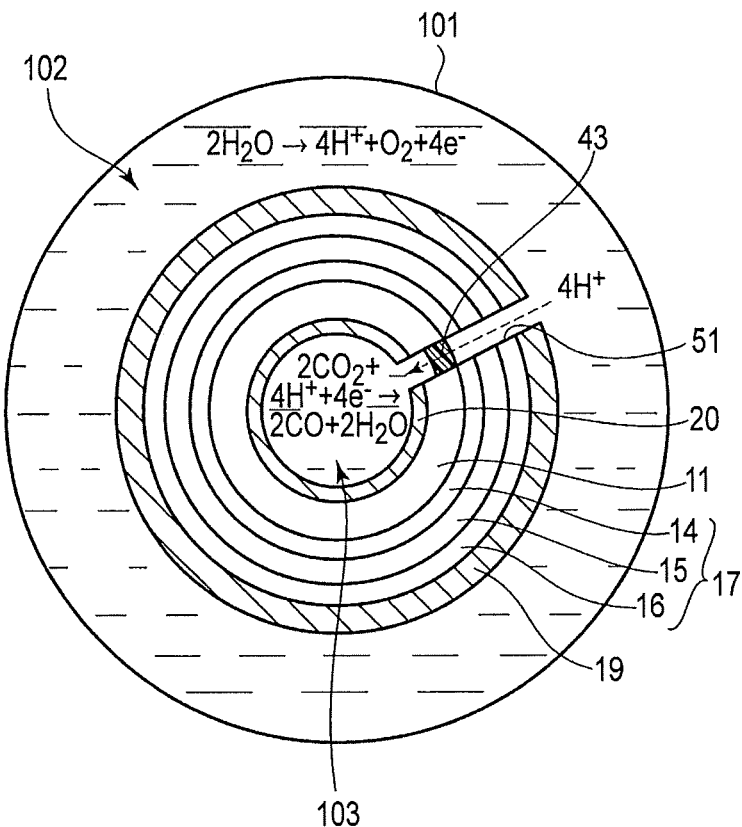
FIG. 25 is a cross-sectional view showing a structure of the photochemical reaction device of the third embodiment.

FIG. 24 is a perspective view showing a structure of the photochemical reaction device of the third embodiment. FIG. 25 is a cross-sectional view showing the structure of the photochemical reaction device of the third embodiment. In FIG. 24, an ion transfer pathway is not shown.

As shown in FIGS. 24 and 25, in the photochemical reaction device of the third embodiment, a piping 101 is used as an electrolytic tank 31. The photovoltaic reaction device of the third embodiment has a photoelectrochemicalcell, a piping 101 including (containing) the photoelectrochemicalcell therein, and an opening 51 formed in a substrate 11, a multi-junction photovoltaic cell 17, an oxidation catalyst layer 19, and a reduction catalyst layer 20 as an ion transfer pathway. In this description, a "piping" means a system of tubes or pipes for leading a fluid.

The photoelectrochemicalcell is formed in a cylindrical (tubular) shape the outer surface of which is the light-irradiation side (the side where the oxidation catalyst layer 19 exists). That is, the photoelectrochemicalcell has a tubular structure to which the oxidation catalyst layer 19, the multi-junction photovoltaic cell 17, the substrate 11, and the reduction catalyst layer 20 are formed from the outer side in this order. This tubular structure divides the piping 101 into two parts along a flow direction. The tubular photoelectrochemicalcell and the tubular piping 101 need not be concentric. In other words, their cross sections need not be concentric. With this arrangement, the piping 101 has an oxidation reaction electrolytic tank 102 on the outer side, to which the oxidation catalyst layer 19 of the photoelectrochemicalcell is disposed, and a reduction reaction electrolytic tank 103 on the inner side, to which the reduction catalyst layer 20 of the photoelectrochemicalcell is disposed. The oxidation reaction electrolytic tank 102 and the reduction reaction electrolytic tank 103 can be provided with different electrolytic solutions. The photoelectrochemicalcell may have a reversed structure, i.e., the reduction catalyst layer 20, the multi-junction photovoltaic cell 17, the substrate 11, and the oxidation catalyst layer 19 are formed from the outer side in this order. In this case, the positions of the oxidation reaction electrolytic tank 102 and the reduction reaction electrolytic tank 103 are also reversed.

The oxidation reaction electrolytic tank 102 is filled with an electrolytic solution, e.g., a liquid including $H_2O$. In the oxidation reaction electrolytic tank 102, $O_2$ and $H^+$ are produced through the oxidation of $H_2O$ by the oxidation catalyst layer 19.

The reduction reaction electrolytic tank 103 is filled with an electrolytic solution, e.g., a liquid including $CO_2$. In the reduction reaction electrolytic tank 103, carbon compounds are produced through the reduction of $CO_2$ by the reduction reaction layer 20.

The opening 51 is formed so as to penetrate the substrate 11, the multi-junction photovoltaic cell 17, the oxidation catalyst layer 19, and the reduction catalyst layer 20 from the side facing the oxidation reaction electrolytic tank 102 to the side facing the reduction reaction electrolytic tank 103. With this arrangement, the opening 51 connects the oxidation reaction electrolytic tank 102 with the reduction reaction electrolytic tank 103.

A portion of the opening 51 is filled with an ion exchange membrane 43, which makes particular ions pass through. This arrangement makes it possible to separate the electrolytic solution in the oxidation reaction electrolytic tank 102 from the electrolytic solution in the reduction reaction electrolytic tank 103 and, at the same time, to make particular ions move via the opening 51 filled with the ion exchange membrane 43. The ion exchange membrane 43 in the above structure is a proton exchange membrane and is able to make $H^+$ produced in the oxidation reaction electrolytic tank 102 move to the reduction reaction electrolytic tank 103.

The photochemical reaction device of the third embodiment is configured with the piping 101. $O_2$ produced in the oxidation reaction electrolytic tank 102 and CO produced in the reduction reaction electrolytic tank 103 can thus be transferred easily by letting them flow through the piping 101 in its flow direction. With this configuration, materials produced by resolving $CO_2$ can be utilized as chemical energy at each facility.

Variations of Third Embodiment

Next, a variation of the photochemical reaction device of the third embodiment will be described below.

Figure 26:
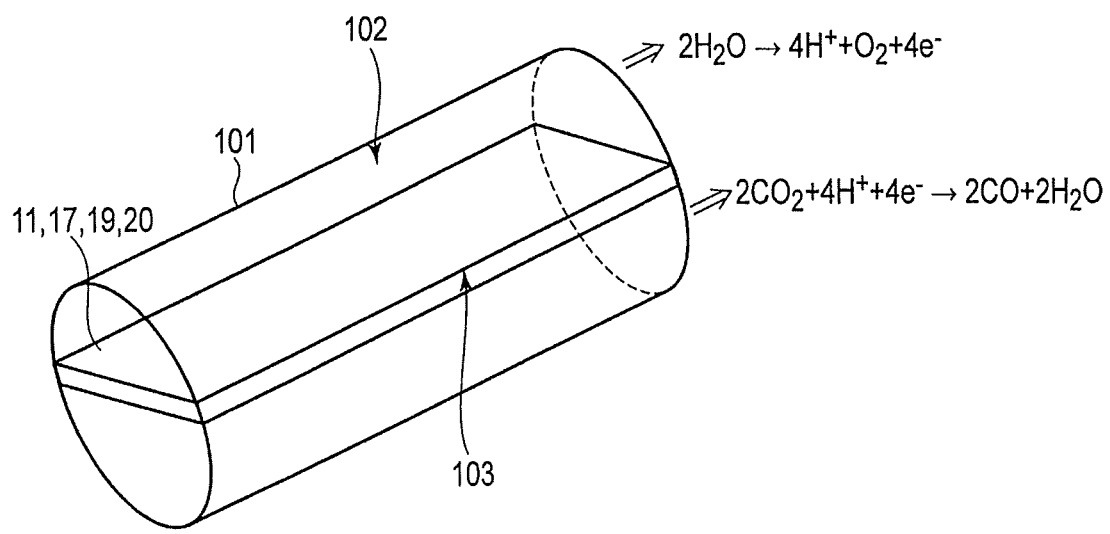
FIG. 26 is a perspective view showing a variation of the structure of the photochemical reaction device of the third embodiment.
Figure 27:
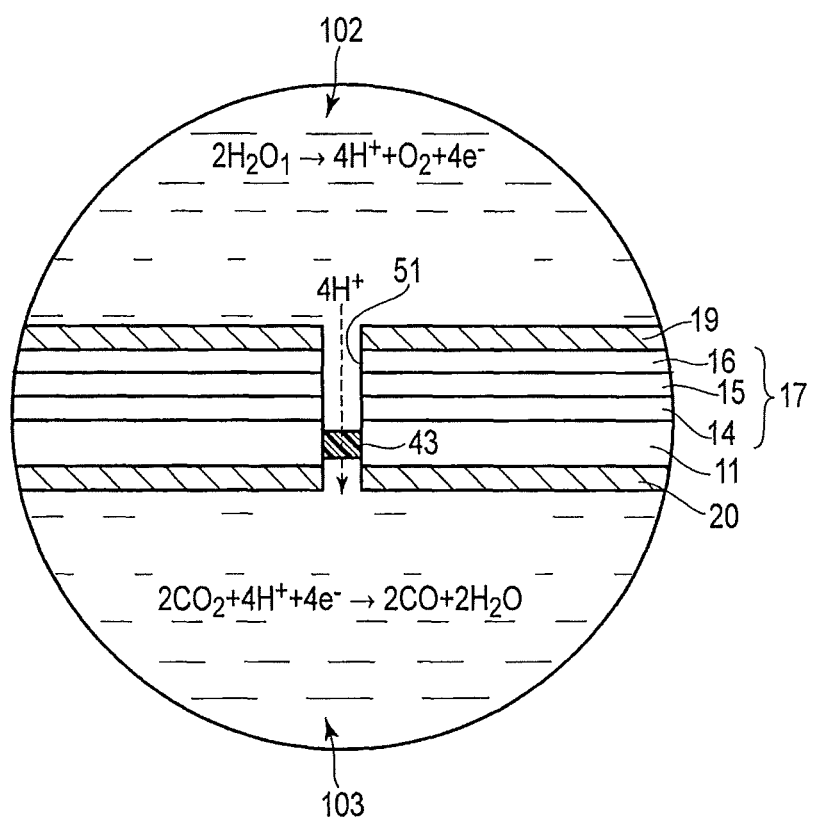
FIG. 27 is a cross-sectional view showing the variation of the structure of the photochemical reaction device of the third embodiment.

FIG. 26 is a perspective view showing a variation of the structure of the photochemical reaction device of the third embodiment. FIG. 27 is a cross-sectional view showing a variation of the structure of the photochemical reaction device of the third embodiment. In FIG. 26, an ion transfer pathway is not shown.

As shown in FIGS. 26 and 27, in the variation of the photochemical reaction device of the third embodiment, the piping 101 is used as the electrolytic tank 31. In the photochemical reaction device of the third embodiment, the photoelectrochemicalcell disposed in the piping 101 is formed in a flat plate-shaped structure. This flat plate-shaped structure divides the piping 101 into two parts along a flow direction. That is, the piping 101 has the oxidation reaction electrolytic tank 102, for example, on the upper side, to which the oxidation catalyst layer 19 of the photoelectrochemicalcell is disposed, and the reduction reaction electrolytic tank 103, for example, on the lower side, to which the reduction catalyst layer 20 of the photoelectrochemicalcell is disposed. The oxidation reaction electrolytic tank 102 and the reduction reaction electrolytic tank 103 can be provided with different electrolytic solutions.

The oxidation reaction electrolytic tank 102 is filled with an electrolytic solution, e.g., a liquid including $H_2O$. In the oxidation reaction electrolytic tank 102, $O_2$ and $H^+$ are produced through the oxidation of $H_2O$ by the oxidation catalyst layer 19.

The reduction reaction electrolytic tank 103 is filled with an electrolytic solution, e.g., a liquid including $CO_2$. In the reduction reaction electrolytic tank 103, carbon compounds are produced through the reduction of $CO_2$ by the reduction reaction layer 20.

The opening 51 is formed so as to penetrate the substrate 11, the multi-junction photovoltaic cell 17, the oxidation catalyst layer 19, and the reduction catalyst layer 20 from the side facing the oxidation reaction electrolytic tank 102 to the side facing the reduction reaction electrolytic tank 103. With this arrangement, the opening 51 connects the oxidation reaction electrolytic tank 102 with the reduction reaction electrolytic tank 103.

A portion of the opening 51 is filled with an ion exchange membrane 43, which makes particular ions pass through. This arrangement makes it possible to separate the electrolytic solution in the oxidation reaction electrolytic tank 102 from the electrolytic solution in the reduction reaction electrolytic tank 103 and, at the same time, to make particular ions move via the opening 51 filled with the ion exchange membrane 43. The ion exchange membrane 43 in the above structure is a proton exchange membrane and is able to make $H^+$ produced in the oxidation reaction electrolytic tank 102 move to the reduction reaction electrolytic tank 103.

Effect of Third Embodiment

By the above-described third embodiment, effects similar to the effects of the first embodiment can be attained.

In the third embodiment, moreover, a photoelectrochemicalcell is applied to a tubular piping. With this structure, it becomes possible to easily transfer chemical compounds produced in the oxidation catalyst layer 19 and the reduction catalyst layer 20 through the piping structure in a flow direction. The produced compounds can be used as chemical energy.

Because the liquid is transferred in a flow, bubbles from the produced gas do not stay on the surfaces of electrodes and electrolytic layers. Because of this feature, the efficiency is not suppressed by sunlight scattering due to bubbles or the light amount distribution can be controlled.

Application Example of Third Embodiment

Next, an application example of the photochemical reaction device of the third embodiment will be described below.

Figure 28:
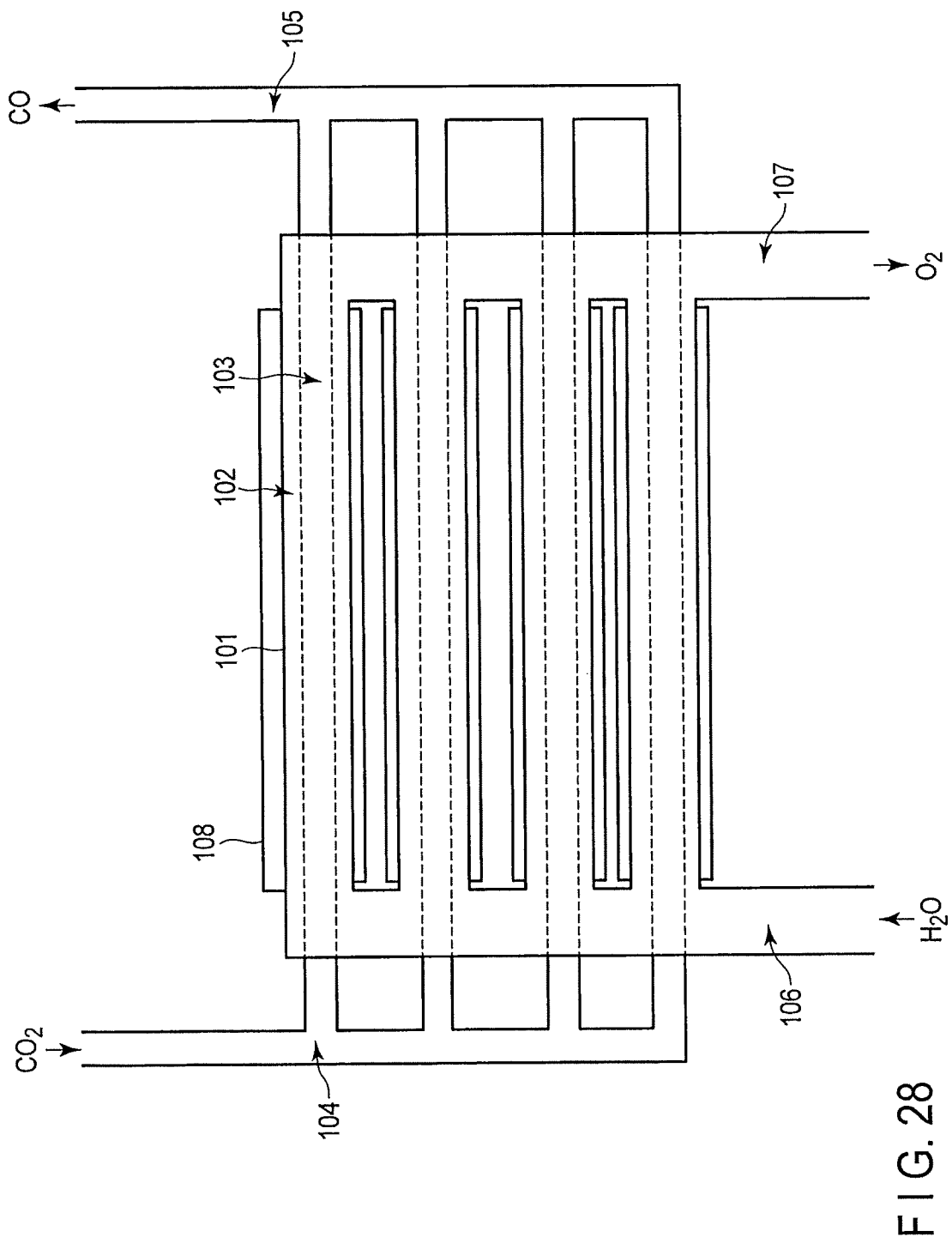
FIG. 28 is a plan view showing an application example of the photochemical reaction device of the third embodiment.

FIG. 28 is a plan view showing an application example of the photochemical reaction device of the third embodiment. More specifically, the example illustrates a case in which the photochemical reaction device of the third embodiment configured as a tubular piping is used as a system.

As shown in FIG. 28, the piping structure has the above-described piping 101 composed of the oxidation reaction electrolytic tank 102 on the outer side and the reduction reaction electrolytic tank 103 on the inner side and a $CO_2$ flow channel 104, an $H_2O$ flow channel 106, a CO flow channel 105, and an $O_2$ flow channel 107 connected therewith.

The $CO_2$ flow channel 104 is connected to one end of the reduction reaction electrolytic tank 103 and the CO flow channel is connected to the other end of the reduction reaction electrolytic tank 103. The $H_2O$ flow channel 106 is connected to one end of the oxidation reaction electrolytic tank 102 and the $O_2$ flow channel 107 is connected to the other end of the oxidation reaction electrolytic tank 102. That is, the reduction reaction electrolytic tank 103 and the oxidation reaction electrolytic tank 102, which compose the piping 101, branch at one end to form the $CO_2$ flow channel 104 and the $H_2O$ flow channel 106, respectively. The reduction reaction electrolytic tank 103 and the oxidation reaction electrolytic tank 102, which compose the piping 101, also branch at the other end to form the CO flow channel 105 and the $O_2$ flow channel 107, respectively.

To the $CO_2$ flow channel 104, $CO_2$ flows in from the outside. In the $CO_2$ flow channel 104, $CO_2$ may flow in a gaseous state or in an electrolytic solution or the like including a $CO_2$ absorbent. The $CO_2$ flow channel 104 is made of a photoelectrochemicalcell that is formed in a tubular shape because the $CO_2$ flow channel 104 is connected (unified) with the reduction reaction electrolytic tank 103. However, the configuration is not limited to this; any configuration with which $CO_2$ in a gaseous state and an electrolytic solution including a $CO_2$ absorbent can flow in may be used.

To the $H_2O$ flow channel 106, $H_2O$ flows in from the outside. In the $H_2O$ flow channel 106, $H_2O$ may flow in a gaseous state or in a liquid state. The $H_2O$ flow channel 106 is made of a structure that is similar to the piping 101 formed in a tubular shape and has a light transmission property because the $H_2O$ flow channel 106 is connected (unified) with the oxidation reaction electrolytic tank 102. However, the configuration is not limited to this; any configuration in which $H_2O$ in a gaseous state and a liquid state can flow may be used.

$H_2O$ which has flowed in from the $H_2O$ flow channel 106 flows in to the oxidation reaction electrolytic tank 102. Then, $H_2O$ is oxidized by the oxidation catalyst layer 19 and $O_2$ and $H^+$ are produced. To the reduction reaction electrolytic tank 103, $CO_2$ which has flowed in from the $CO_2$ flow channel 104 flows in. Then, $CO_2$ is reduced by the reduction catalyst layer 20 and carbon compounds (CO or the like) are produced.

The CO flow channel 105 makes the carbon compound such as CO produced in the reduction reaction electrolytic tank 103 flow out to the outside. In the CO flow channel 105, CO may flow out in a gaseous state or in a liquid state. The CO flow channel 105 is connected to the other end of the reduction reaction electrolytic tank 103. The CO flow channel 105 is thus configured with a photoelectrochemicalcell formed in a tubular structure. However, any structure by which CO in a gaseous state or a liquid state can flow out may be used.

The $O_2$ flow channel 107 makes $O_2$ produced in the oxidation reaction electrolytic tank 102 flow out to the outside. In the $O_2$ flow channel 107, $O_2$ may flow out in a gaseous state or in a liquid state. The $O_2$ flow channel 107 is connected to the other end of the oxidation reaction electrolytic tank 102. The $O_2$ flow channel 107 is thus configured with a structure similar to the tubular piping 101 with a light transmission property. However, any structure by which $O_2$ in a gaseous state or a liquid state can flow out may be used.

A reflector 108 may be disposed on the light emitting surface side of the piping 101. The reflector 108 is, for example, a concave mirror disposed in the tubular piping 101, which can reflect light and make it reenter the piping 101. With this configuration, the photochemical reaction efficiency can be improved. Moreover, reflective conditions can be changed by filling the piping 101 with a liquid. With this configuration, the photochemical reaction efficiency can also be improved by making light enter the piping 101 by reflection and refraction at the piping 101 or the gas-liquid interface.

As described above, using the photochemical reaction device of the third embodiment, which is a tubular piping, it is possible to resolve $CO_2$ which flows in from the outside and to make materials from the resolution flow out separately on the reduction side and the oxidation side.

3. Photochemical Reaction System

Referring to FIG. 29 to FIG. 34, a photochemical reaction system of the embodiment will be described below. The photochemical reaction system of the embodiment can be designed, for example, using a piping structure shown in FIG. 28.

Figure 29:
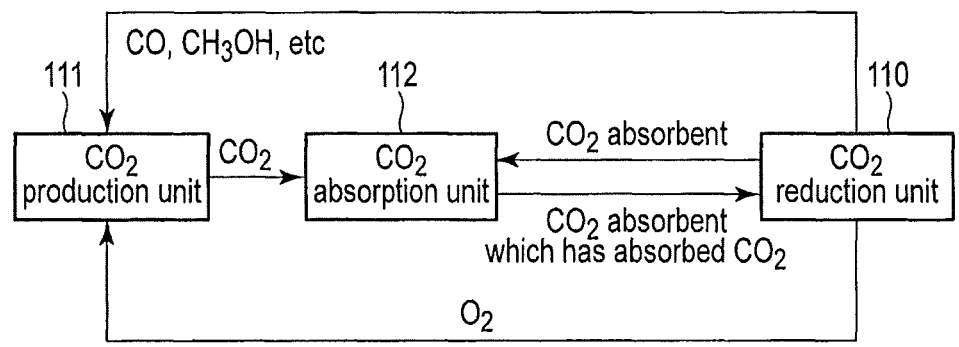
FIG. 29 is a block diagram showing a configuration of a photochemical reaction system of the embodiment.

FIG. 29 is a block diagram showing a configuration of the photochemical reaction system of the embodiment;

As shown in FIG. 29, the photochemical reaction system has a $CO_2$ reduction unit 110, a $CO_2$ production unit 111, and a $CO_2$ absorption unit 112.

The $CO_2$ reduction unit 110 is, for example, the above-described photochemical reaction device. The $CO_2$ reduction unit 110 makes an electrolytic solution containing a $CO_2$ absorbent flow out to the $CO_2$ absorption unit 112 and makes an electrolytic solution containing a $CO_2$ absorbent which has absorbed $CO_2$ from the $CO_2$ absorption unit 112 flow in. The $CO_2$ reduction unit 110 also produces carbon compounds such as CO, HCOOH, $CH_3OH$, and $CH_4$ by reducing $CO_2$ absorbed by a $CO_2$ absorbent and makes them flow out to the $CO_2$ production unit 111. The $CO_2$ reduction unit 110 further produces $O_2$ by oxidizing $H_2O$ along with the $CO_2$ reduction and makes it flow out to the $CO_2$ production unit 111.

The $CO_2$ production unit 111 is, for example, a power plant. The $CO_2$ production unit 111 makes carbon compounds such as CO, HCOOH, $CH_3OH$, and $CH_4$ which are produced by the $CO_2$ reduction unit 110 flow in. The $CO_2$ production unit 111 produces $CO_2$ together with acquiring energy by burning a carbon fuel such as $CH_3OH$, and $CH_4$. The $CO_2$ production unit 111 makes the produced $CO_2$ flow out to the $CO_2$ absorption unit 112. The $CO_2$ production unit 111 also makes $O_2$ produced by the $CO_2$ production unit 111 flow in. By using this $O_2$ as a combustion improver, the combustion efficiency of the carbon fuel can be improved to decrease the total emission of $CO_2$.

The $CO_2$ absorption unit 112 is, for example, CCS (Carbon Dioxide Capture and Storage). The $CO_2$ absorption unit 112 absorbs $CO_2$ produced by the $CO_2$ production unit 111 using a $CO_2$ absorbent made flow in from the $CO_2$ reduction unit 110. With this process, the $CO_2$ absorption unit 112 collects and stores $CO_2$. The $CO_2$ absorption unit 112 makes an electrolytic solution containing a $CO_2$ absorbent which has absorbed $CO_2$ flow out to the $CO_2$ reduction unit 110.

As described above, the photochemical system of the embodiment produces $CO_2$ along with acquiring energy by burning carbon fuel in the $CO_2$ production unit 111, absorbs $CO_2$ produced by the $CO_2$ reduction unit 112, and reductively decomposes $CO_2$ by the $CO_2$ reduction unit 110. The photochemical reaction system makes carbon compounds produced by the $CO_2$ reduction unit 110 together with the reductive decomposition of $CO_2$ flow out again to the $CO_2$ production unit 111 as a carbon fuel. By this process, $CO_2$ can be decomposed efficiently and energy can also be acquired efficiently using products produced by the decomposition.

The $CO_2$ production unit 111 which emits $CO_2$ by burning carbon fuel includes not only a power plant but also an ironworks, chemical plant, waste disposal facility, etc. The above described system is suitable for an ironworks because an ironworks requires high temperatures, causes high $CO_2$ emissions, consumes $O_2$. The system is also suitable for a chemical plant because a chemical plant requires all of energy, carbon compounds, and $O_2$.

Supplying living things such as fish in a fishery with $O_2$ produced by the $CO_2$ reduction unit 110 has effects of promoting their growth and preventing their disease. It is possible to reduce $CO_2$ emitted from living things by the $CO_2$ reduction unit 110 and to supply the living things with the produced $O_2$. It is also possible to acquire energy such as heat and electricity by burning carbon compounds produced through reducing $CO_2$ as a carbon fuel by the $CO_2$ production unit 111. It is further possible to supply the energy to the fishery again.

The efficiency in sewage treatment can be improved by supplying bacteria or the like for sewage treatment with $O_2$ produced by the $CO_2$ reduction unit 110. Similarly, energy such as heat and electricity can be acquired by burning carbon compounds produced through $CO_2$ reduction as a carbon fuel. It is further possible to supply the energy to the sewage treatment plant again. With this arrangement, an operational cost of a sewage treatment plant can be reduced. Moreover, carbon compounds such as $CH_3OH$, $C_2H_5OH$, and $CH_4$ may be produced with bacteria by using $H_2$ produced by the $CO_2$ reduction unit 110 together with the reductive decomposition of $CO_2$.

$O_2$ produced by the $CO_2$ reduction unit 110 may be supplied to hospitals. Similarly, energy such as heat and electricity may be acquired by burning carbon compounds produced through $CO_2$ reduction as a carbon fuel by the $CO_2$ production unit 111 and supplied to hospitals. Furthermore, chemical energy may be acquired by supplying $CO_2$ created by in-house power generation to the $CO_2$ reduction unit 110 again.

$O_2$ may be usable as an oxidizing power for an air cleaning system, a water purification system, or a system cleansing a contaminated organic substance. The acquired energy may be recycled by using the energy for system operation, absorbing the $CO_2$ produced in supplying the system with energy, and converting the $CO_2$ to chemical energy again by the $CO_2$ reduction unit 110 and the $CO_2$ production unit 111.

Figure 30:
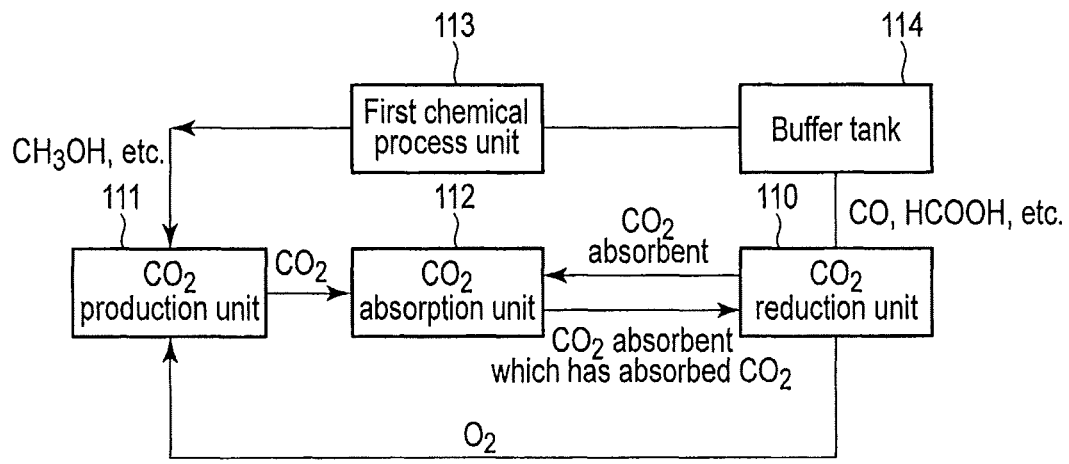
FIG. 30 is a block diagram showing a configuration of variation 1 of the photochemical reaction system of the embodiment.
Figure 31:
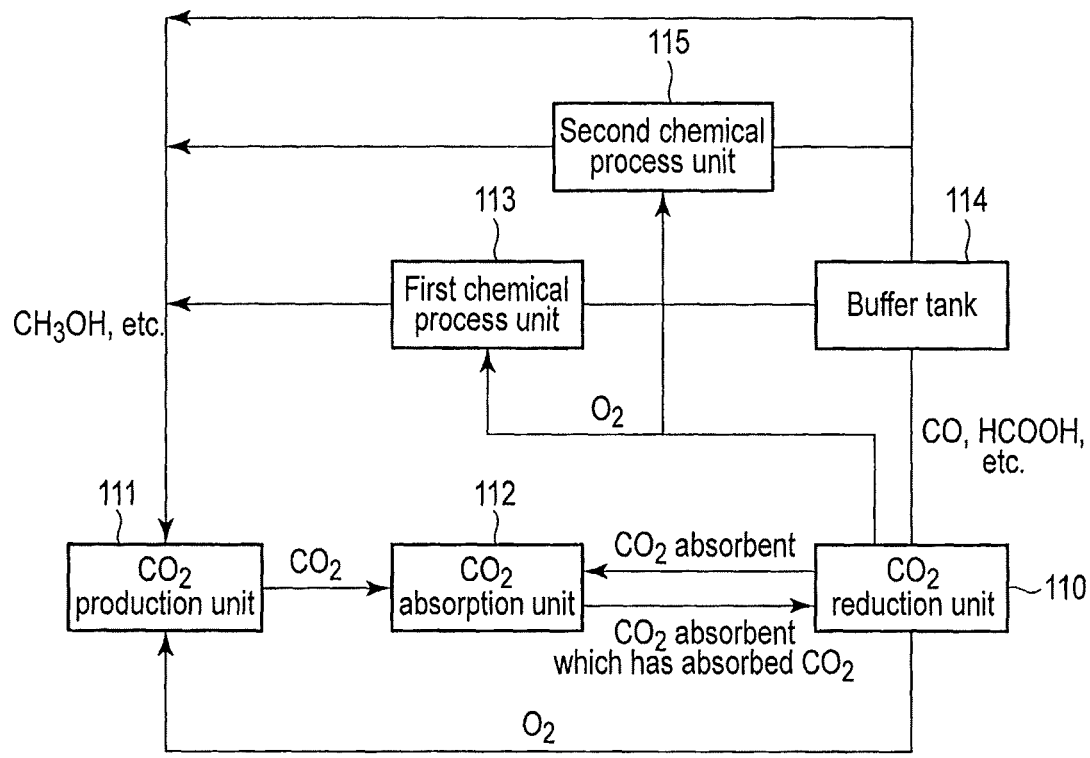
FIG. 31 is a block diagram showing a configuration of variation 2 of the photochemical reaction system of the embodiment.
Figure 32:
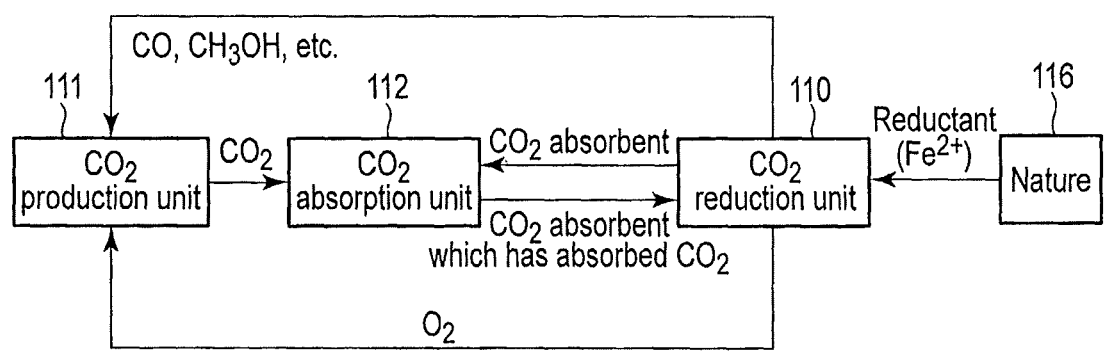
FIG. 32 is a block diagram showing a configuration of variation 3 of the photochemical reaction system of the embodiment.

FIG. 30 is a block diagram showing a configuration of variation 1 of the photochemical reaction system of the embodiment. FIG. 31 is a block diagram showing a configuration of variation 2 of the photochemical reaction system of the embodiment. FIG. 32 is a block diagram showing a configuration of variation 3 of the photochemical reaction system of the embodiment.

Although it is possible to produce CO or HCOOH by decomposing $CO_2$ with the $CO_2$ reduction unit 110 (the reduction catalyst layer 20), producing $CH_3OH$, $CH_4$ or the like, which is used as a carbon fuel, at once is difficult. More specifically, it is necessary to produce CO or HCOOH first with the $CO_2$ reduction unit 110 and, then, convert such to $CH_3OH$, $CH_4$ or the like.

In contrast to this, the photochemical reaction system in variation 1 has a first chemical process unit 113 and a buffer tank 114 as shown in FIG. 30.

The first chemical process unit 113 and the buffer tank 114 are disposed in a flow channel between the $CO_2$ reduction unit 110 and the $CO_2$ production unit 111. The first chemical process unit 113 produces $CH_3OH$, $CH_4$ or the like by causing a chemical reaction of CO or HCOOH produced by the $CO_2$ reduction unit 110. That is, the first chemical process unit 113 conducts an intermediate treatment in the production of carbon fuel. In this process, it is desirable to adjust the ratios of CO and $H_2$ produced by the $CO_2$ reduction unit 110 to values that are appropriate for the first chemical process unit 113 by regulating the chemical structure of and the amount of water in an electrolytic solution. In the case of producing $CH_3OH$, for example, the reaction progresses according to the following formula (3).

$$CO+H_2 \rightarrow CH_3OH \quad (3)$$

As shown by the formula (3), if $CH_3OH$ is produced from CO and $H_2$, the reaction stoichiometrically progresses with CO:H=1:2. Thus, it is desirable that the ratios of CO and $H_2$ produced by the $CO_2$ reduction unit 110 are adjusted to the above ratio.

Although a ratio different from the above value may often be used because energy efficiency and cost are taken into consideration, adjusting the ratio to an appropriate value is possible.

Products may change depending on a device temperature, intensity of light, or change in wavelength. In order to cope with these changes, the buffer tank 114 is arranged.

In the case that the $CO_2$ reduction unit 110 uses sunlight energy, dealing with long-term changes due to the rainy season or the like causes a problem such as increase in size of the buffer tank 114.

The photochemical reaction system in the variation 2, in contrast, further has a second chemical process unit 115 as shown in FIG. 31.

The second chemical process unit 115 is disposed in a flow channel between the $CO_2$ reduction unit 110 and the $CO_2$ production unit 111 and disposed another flow channel different from the first chemical process unit 113. The second chemical process unit 115 uses different manufacturing device and a different method from that used in the first chemical process unit 113.

As described above, fluctuations in chemical reaction due to weather conditions or temperature conditions may be controlled by having the first chemical process unit 113 and the second chemical process unit 115 as different flow channels and switching an active flow channel between them appropriately.

Reaction conditions and products of the first chemical process unit 113 and second chemical process unit 115 can be changed. Such change may depend on the tank volume of a product from each of the first chemical process unit 113 and the second chemical process unit 115. $O_2$ produced by the $CO_2$ reduction unit 110 may be supplied to them. The combination of these units is an example and there is no constraint to a combination with a plurality of chemical process units or processes of multiple stages. The reflection condition can be changed by varying the angle and position of the reflector 108 or changing the amount of liquid in the piping. With this arrangement, the amount of light incident on the piping 101 can be changed through reflection and refraction at the piping or gas-liquid interface. Accordingly, the photochemical reaction efficiency can be improved and products can selectively be reproduced.

In the photoelectrochemicalcell in the $CO_2$ reduction unit 110, irradiation of sunlight causes charge separation in the multi-junction photovoltaic cell 17 and the charge separation leads to the production of $H^+$ and $O_2$ through the oxidation of $H_2O$ by the oxidation catalyst layer 19. In this process, electrons move to the opposite reduction catalyst layer 20 due to the oxidation reaction by the oxidation catalyst layer 19. By these moved electrons, the reduction reaction of $CO_2$ by the reduction catalyst layer 20 progresses. However, a huge amount of energy is necessary to oxidize $H_2O$. There is thus a large potential difference between the oxidation potential of $H_2O$ and the reduction potential of $CO_2$. Therefore, an oxidation reaction of $H_2O$ and a reduction reaction of $CO_2$ require so much energy that carrying out both reactions is very difficult.

An example in which, as an electron source (reductant) of the oxidation catalyst layer 19, a sacrificial reagent such as a triethanolamine is used is known. It is possible to reduce the potential difference between the oxidation reaction and reduction reaction by using a reductant such as a sacrificial reagent as a substitute of a reaction decomposing $H_2O$ into $H^+$ and $O_2$ by the oxidation catalyst layer 19. By this method, the oxidation reaction and reduction reaction may progress with relative ease. As a result, it becomes possible to decrease the number of junctions of multi-junction photovoltaic cells and to compose a photovoltaic cell in a single layer. Even in the case of using a conventional photovoltaic cell, the reaction may progress further due to a current increase. Any of these combinations can be chosen depending on the potential difference between the oxidation reaction and the reduction reaction, the output power of a substitute cell, or a combination of catalysts. It is also possible to prevent a decreased reaction caused by a change of weather and to produce a different product by varying a sacrificial reagent such as a triethanolamine as an electron source (reductant) of the reduction catalyst layer 19, supplying triethanolamine in aqueous solution and varying its concentration, or replacing triethanolamine with water.

As shown in FIG. 32, in the photochemical reaction system of variation 3, as a reductant which reduces the potential difference in an oxidation-reduction reaction, a reductant which can be acquired from nature 116 is used. A reductant means a substance that has a reducing power. In other words, a reductant is a substance that loses an electron by being oxidized and reduces other substances with the electron.

Such a reductant available in nature 116 includes a divalent ion of iron ($Fe^{2+}$) which is included in, for example, drainage from a mine. Any reductant which exists in nature, such as hydrogen sulfide and sulfur, is usable. In the photochemical reaction system of variation 3, $Fe^{2+}$, which is available in nature 116, is used as a reductant for the reaction at the oxidation catalyst layer 19 in the $CO_2$ reduction unit 110. The chemical reaction in the photoelectrochemicalcell used in the $CO_2$ reduction unit 110 will be described in detail below.

Figure 33:
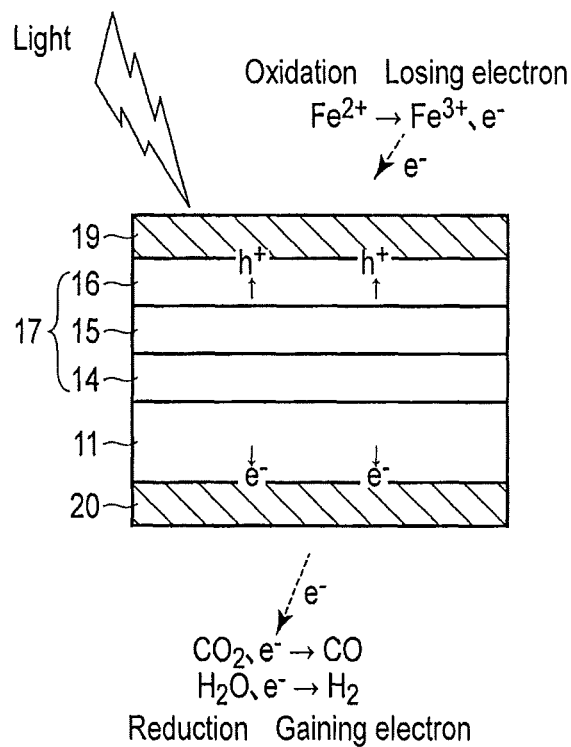
FIG. 33 is a cross-sectional view showing an operating principle of a photoelectrochemicalcell in variation 3 of the photochemical reaction system of the embodiment.

FIG. 33 is a cross-sectional view illustrating an operating principle of the photoelectrochemicalcell in variation 3 of the photochemical reaction system of the embodiment. In FIG. 33, the reflecting layer 12, the reduction electrode layer 13, and the oxidation electrode layer 18 are not shown.

As shown in FIG. 33, $Fe^{2+}$ acquired from nature is oxidized (losing an electron) and a trivalent ion of iron ($Fe^{3+}$) is produced in the vicinity of the oxidation catalyst layer 19. The electron produced in the oxidation reaction moves to the reduction catalyst layer 20. In the vicinity of the reduction catalyst layer 20, a reduction reaction takes place by the moved electron. More specifically, CO is produced by reducing $CO_2$ and $H_2$ is produced by reducing $H_2O$.

In the reduction process, the potential difference between the oxidation reaction of $Fe^{2+}$ and the reduction reaction of $CO_2$ or $H_2O$ is small. Therefore, it is possible to drive the oxidation reaction and reduction reaction with relative ease.

The above-described $Fe^{2+}$ is abundant in mines over the world and a much can be found in mine drainage containing sulphur. Sulphuric acid water with a low pH produced through the oxidation of sulphur in tunnels has therefore become an environmental problem. In particular, $Fe^{2+}$ needs to be neutralized with a neutralizer such as inexpensive calcium carbonate. $Fe^{2+}$, however, is unreactive with calcium carbonate. Using energy by use of bacteria in order to oxidize $Fe^{2+}$ to $Fe^{3+}$ is also a problem.

In variation 3 of the photochemical reaction system of the embodiment, mine wastewater, which contains $Fe^{2+}$ acquirable from nature 116, is used as an electrolytic solution at the oxidation catalyst layer 19. With this $Fe^{2+}$ used as a reductant, an energetic material such as $H_2$ and CO can easily be acquired with the reduction catalyst layer 20. At the same time, it becomes possible to oxidize $Fe^{2+}$ in nature 116 and solve the environmental problem caused by $Fe^{2+}$.

Using the energy acquired by the above-described method as the energy for mining or a mine wastewater treatment facility is more preferable in that there are few losses in energy transfer.

Figure 34:
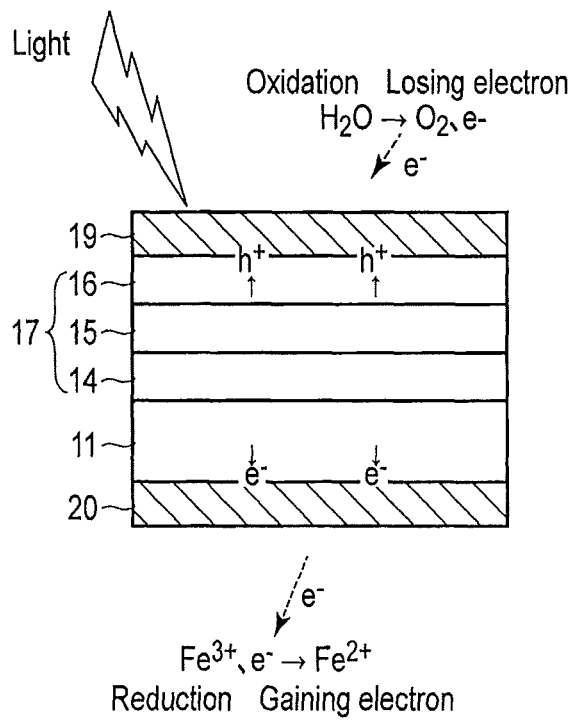
FIG. 34 is a cross-sectional view showing another operating principle of the photoelectrochemicalcell in variation 3 of the photochemical reaction system of the embodiment.

As shown in FIG. 34, reducing ferric hydroxide ($Fe(OH)_3$), which has become $Fe^{3+}$ and precipitated, as an electrolytic solution at the reduction catalyst layer 20 is also effective. Producing $Fe^{2+}$ with this method and using it as an electrolytic solution at the oxidation catalyst layer 19 again makes it possible to recycle $Fe^{2+}$ as a reductant.

FIG. 35 is a block diagram showing a configuration of variation 4 of the photochemical reaction system of the configuration.

As shown in FIG. 35, the photochemical reaction system in variation 4 further has a $CO_2$ release unit 121 and a $CO_2$ storage unit 122.

The $CO_2$ release unit 121 makes an electrolytic solution containing a $CO_2$ absorbent which has absorbed $CO_2$ from the $CO_2$ absorption unit 112 flow in. The $CO_2$ release unit 121 decomposes the $CO_2$ absorbent which has absorbed $CO_2$ into $CO_2$ and a $CO_2$ absorbent. That is, the $CO_2$ release unit 121 can extract only $CO_2$ from a $CO_2$ absorbent which has absorbed $CO_2$. The $CO_2$ release unit 121 makes the decomposed $CO_2$ flow out to the $CO_2$ storage unit 122. The $CO_2$ release unit 121 also makes the decomposed $CO_2$ absorbent flow out to the $CO_2$ reduction unit 110.

The $CO_2$ storage unit 122 is, for example, underground or the ocean floor. The $CO_2$ storage unit 122 makes $CO_2$ flow in from the $CO_2$ release unit 121 and stores it. That is, $CO_2$ decomposed in the $CO_2$ release unit 121 is buried in the $CO_2$ storage unit 122 such as underground or ocean floor. $CO_2$ stored in the $CO_2$ storage unit 122 may be made flow out to the $CO_2$ reduction unit 110 and reduced by the $CO_2$ reduction unit 110.

It is difficult, in general, to decompose a $CO_2$ absorbent which has absorbed $CO_2$ to $CO_2$ and a $CO_2$ absorbent completely in the $CO_2$ release unit 121. Therefore, if the $CO_2$ release unit 121 makes a $CO_2$ absorbent retaining $CO_2$ partially flow out to the $CO_2$ absorption unit 112 and the $CO_2$ absorption unit 112 uses the $CO_2$ absorbent retaining $CO_2$ partially in order to absorb $CO_2$ released from the $CO_2$ production unit 111, an energy loss and efficiency loss are generated.

In variation 4, the $CO_2$ release unit 121 may make a $CO_2$ absorbent retaining $CO_2$ partially flow out to the $CO_2$ reduction unit 110. That is, the $CO_2$ reduction unit 110 makes an electrolytic solution containing a $CO_2$ absorbent which has absorbed $CO_2$ partially from the $CO_2$ release unit 121 flow in. The $CO_2$ reduction unit produces carbon compounds such as CO, HCOOH, $CH_3OH$, and $CH_4$ by reducing part of the $CO_2$ absorbed by a $CO_2$ absorbent and makes them flow out to the $CO_2$ production unit 111. The $CO_2$ reduction unit 110 further produces $O_2$ by oxidizing $H_2O$ along with the $CO_2$ reduction and makes it flow out to the $CO_2$ production unit 111. The rest of a $CO_2$ absorbent from which $CO_2$ is reduced partially by the $CO_2$ reduction unit 110 is made to flow in to the $CO_2$ absorption unit 112 again and reused for $CO_2$ absorption in the $CO_2$ absorption unit 112.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A chemical reaction system, comprising:
   a $CO_2$ reduction unit comprising: an oxidation catalyst layer producing $O_2$ and $H^+$ by oxidizing $H_2O$; a reduction catalyst layer producing carbon compounds by reducing $CO_2$; and an ion transfer pathway making ions to move between the oxidation catalyst layer and the reduction catalyst layer;
   a $CO_2$ release unit which forms $CO_2$ by decomposing a $CO_2$ absorbent which has absorbed $CO_2$ and makes the decomposed $CO_2$ absorbent flow out to the $CO_2$ reduction unit; and
   a $CO_2$ storage unit storing the $CO_2$ decomposed by the $CO_2$ release unit.

2. The system of claim 1, wherein the $CO_2$ storage unit supplies the stored $CO_2$ to the $CO_2$ reduction unit.

3. The system of claim 1, wherein the decomposed $CO_2$ absorbent comprises $CO_2$, and the $CO_2$ reduction unit reduces the $CO_2$ contained in the decomposed $CO_2$ absorbent.

* * * * *